(12) United States Patent
Badstibner et al.

(10) Patent No.: US 8,764,621 B2
(45) Date of Patent: Jul. 1, 2014

(54) TRANSCUTANEOUS POWER TRANSMISSION AND COMMUNICATION FOR IMPLANTED HEART ASSIST AND OTHER DEVICES

(75) Inventors: Kurt D. Badstibner, North Versailles, PA (US); Jonathan R. Speicher, Pittsburgh, PA (US); Marlin S. Heilman, Saver, PA (US); Richard A. Bates, Allison Park, PA (US); Charles E. Greene, Cabot, PA (US)

(73) Assignee: Vascor, Inc., Pittsburgh, PA (US)

( * ) Notice: Subject to any disclaimer, the term of this patent is extended or adjusted under 35 U.S.C. 154(b) by 21 days.

(21) Appl. No.: 13/546,789

(22) Filed: Jul. 11, 2012

(65) Prior Publication Data

US 2013/0289334 A1     Oct. 31, 2013

Related U.S. Application Data

(60) Provisional application No. 61/506,621, filed on Jul. 11, 2011.

(51) Int. Cl.
*A61N 1/362*     (2006.01)

(52) U.S. Cl.
USPC .......................................................... 600/16

(58) Field of Classification Search
None
See application file for complete search history.

(56) References Cited

U.S. PATENT DOCUMENTS

| | | |
|---|---|---|
| 4,352,960 A | 10/1982 | Dormer |
| 4,408,607 A | 10/1983 | Maurer |
| 4,679,560 A | 7/1987 | Galbraith |
| 4,741,339 A | 5/1988 | Harrison |
| RE32,947 E | 6/1989 | Dormer |
| 4,925,443 A | 5/1990 | Heilman |
| 5,279,292 A | 1/1994 | Baumann |
| 5,314,457 A | 5/1994 | Jeutter |
| 5,591,217 A | 1/1997 | Barreras |
| 5,617,871 A | 4/1997 | Burrows |
| 5,630,836 A | 5/1997 | Prem |
| 5,676,162 A | 10/1997 | Larson, Jr. |
| 5,690,693 A | 11/1997 | Wang |
| 5,702,431 A | 12/1997 | Wang |
| 5,713,939 A | 2/1998 | Nedungadi |
| 5,735,887 A | 4/1998 | Barreras, Sr. |
| 5,741,316 A | 4/1998 | Chen |
| 5,755,748 A | 5/1998 | Borza |
| 5,769,877 A | 6/1998 | Barreras, Sr. |
| 5,807,397 A | 9/1998 | Barreras |

(Continued)

FOREIGN PATENT DOCUMENTS

| | | |
|---|---|---|
| AU | 2010200044 A1 | 1/2010 |
| CA | 2615123 A1 | 1/2007 |

(Continued)

*Primary Examiner* — Brian T Gedeon
(74) *Attorney, Agent, or Firm* — Bartony & Associates, LLC

(57) ABSTRACT

A system includes an implantable pump system for assisting blood flow in a patient including at least one movable valve. The movable valve is in a normally open state when the moveable valve is not being powered and a drive system in operative connection with the moveable valve to move the moveable valve under power. The system further includes an energy transfer system to provide energy to the drive system. The energy transfer system includes an external system including a power source and an external coil and an internal system including an internal coil adapted to receive transcutaneous energy transmitted from the external coil. The internal system has at least a first state wherein energy transmission from the external coil is required to provide operational power to the drive system.

42 Claims, 16 Drawing Sheets

(56) References Cited

U.S. PATENT DOCUMENTS

| | | |
|---|---|---|
| 5,991,664 A | 11/1999 | Seligman |
| 5,995,874 A | 11/1999 | Borza |
| 6,058,330 A | 5/2000 | Borza |
| 6,099,495 A | 8/2000 | Kinghorn |
| 6,240,318 B1 | 5/2001 | Phillips |
| 6,275,737 B1 | 8/2001 | Mann |
| 6,473,652 B1 | 10/2002 | Sarwal |
| 6,772,011 B2 | 8/2004 | Dolgin |
| 6,850,803 B1 | 2/2005 | Jimenez |
| 7,114,502 B2 | 10/2006 | Schulman |
| 7,171,273 B2 | 1/2007 | Shaquer |
| 7,225,032 B2 | 5/2007 | Schmeling |
| 7,286,880 B2 | 10/2007 | Olson |
| 7,286,881 B2 | 10/2007 | Schommer |
| 7,308,316 B2 | 12/2007 | Schommer |
| 7,428,438 B2 | 9/2008 | Parramon |
| 7,505,816 B2 | 3/2009 | Schmeling |
| 7,512,443 B2 | 3/2009 | Phillips |
| 7,515,967 B2 | 4/2009 | Phillips |
| 7,571,007 B2 | 8/2009 | Erickson |
| 7,588,530 B2 | 9/2009 | Heilman |
| 7,599,744 B2 | 10/2009 | Giordano |
| 7,741,734 B2 | 6/2010 | Joannopoulos |
| 7,774,069 B2 | 8/2010 | Olson |
| 7,825,543 B2 | 11/2010 | Karalis |
| 7,857,766 B2 | 12/2010 | Lasater |
| 7,945,334 B2 | 5/2011 | Jimenez |
| 8,005,547 B2 | 8/2011 | Forsberg |
| 2002/0177884 A1 | 11/2002 | Ahn |
| 2005/0075693 A1 | 4/2005 | Toy |
| 2005/0075694 A1 | 4/2005 | Schmeling |
| 2005/0075696 A1 | 4/2005 | Forsberg |
| 2005/0075697 A1 | 4/2005 | Olson |
| 2005/0075699 A1 | 4/2005 | Olson |
| 2005/0113888 A1 | 5/2005 | Jimenez |
| 2005/0113889 A1 | 5/2005 | Jimenez |
| 2005/0119716 A1 | 6/2005 | McClure |
| 2005/0131495 A1 | 6/2005 | Parramon |
| 2006/0161225 A1 | 7/2006 | Sormann |
| 2006/0247737 A1 | 11/2006 | Olson |
| 2006/0247738 A1 | 11/2006 | Schmeling |
| 2006/0259098 A1 | 11/2006 | Erickson |
| 2007/0118185 A1 | 5/2007 | Shaquer |
| 2007/0167997 A1 | 7/2007 | Forsberg |
| 2008/0051855 A1 | 2/2008 | Schommer |
| 2008/0278264 A1 | 11/2008 | Karalis |
| 2009/0157148 A1 | 6/2009 | Phillips |
| 2009/0195333 A1 | 8/2009 | Joannopoulos |
| 2009/0210035 A1 | 8/2009 | Gelbart |
| 2009/0224856 A1 | 9/2009 | Karalis |
| 2009/0267709 A1 | 10/2009 | Joannopoulos |
| 2009/0267710 A1 | 10/2009 | Joannopoulos |
| 2009/0270951 A1 | 10/2009 | Kallmyer |
| 2009/0284083 A1 | 11/2009 | Karalis |
| 2010/0063347 A1 | 3/2010 | Yomtov |
| 2010/0076524 A1 | 3/2010 | Forsberg |
| 2010/0096934 A1 | 4/2010 | Joannopoulos |
| 2010/0102639 A1 | 4/2010 | Joannopoulos |
| 2010/0102640 A1 | 4/2010 | Joannopoulos |
| 2010/0102641 A1 | 4/2010 | Joannopoulos |
| 2010/0109445 A1 | 5/2010 | Kurs |
| 2010/0117455 A1 | 5/2010 | Joannopoulos |
| 2010/0117456 A1 | 5/2010 | Karalis |
| 2010/0123353 A1 | 5/2010 | Joannopoulos |
| 2010/0123354 A1 | 5/2010 | Joannopoulos |
| 2010/0123355 A1 | 5/2010 | Joannopoulos |
| 2010/0127573 A1 | 5/2010 | Joannopoulos |
| 2010/0127574 A1 | 5/2010 | Joannopoulos |
| 2010/0127575 A1 | 5/2010 | Joannopoulos |
| 2010/0133918 A1 | 6/2010 | Joannopoulos |
| 2010/0133919 A1 | 6/2010 | Joannopoulos |
| 2010/0133920 A1 | 6/2010 | Joannopoulos |
| 2010/0141042 A1 | 6/2010 | Kesler |
| 2010/0148589 A1 | 6/2010 | Hamam |
| 2010/0164296 A1 | 7/2010 | Kurs |
| 2010/0164297 A1 | 7/2010 | Kurs |
| 2010/0164298 A1 | 7/2010 | Karalis |
| 2010/0171368 A1 | 7/2010 | Schatz |
| 2010/0181843 A1 | 7/2010 | Schatz |
| 2010/0181845 A1 | 7/2010 | Fiorello |
| 2010/0187911 A1 | 7/2010 | Joannopoulos |
| 2010/0211134 A1 | 8/2010 | Forsell |
| 2010/0217352 A1 | 8/2010 | Forsell |
| 2010/0217353 A1 | 8/2010 | Forsell |
| 2010/0222848 A1 | 9/2010 | Forsell |
| 2010/0222849 A1 | 9/2010 | Forsell |
| 2010/0233958 A1 | 9/2010 | Washiro |
| 2010/0234922 A1 | 9/2010 | Forsell |
| 2010/0256709 A1 | 10/2010 | Kallmyer |
| 2010/0268305 A1 | 10/2010 | Olson |
| 2011/0022125 A1 | 1/2011 | Olson |
| 2011/0196452 A1 | 8/2011 | Forsell |
| 2011/0196466 A1 | 8/2011 | Forsell |
| 2011/0230930 A1 | 9/2011 | Forsell |
| 2011/0298420 A1 | 12/2011 | Forsberg |
| 2011/0301667 A1 | 12/2011 | Olson |
| 2011/0301668 A1 | 12/2011 | Forsell |
| 2011/0301669 A1 | 12/2011 | Olson |
| 2012/0053657 A1 | 3/2012 | Parker |
| 2013/0041203 A1 | 2/2013 | Heilman |
| 2013/0041204 A1 | 2/2013 | Heilman |
| 2013/0041460 A1 | 2/2013 | Heilman |

FOREIGN PATENT DOCUMENTS

| | | |
|---|---|---|
| EP | 2302756 A1 | 3/2011 |
| KR | 1020080031398 | 4/2008 |
| WO | WO2007008646 A2 | 1/2007 |
| WO | WO2008118178 A1 | 10/2008 |
| WO | WO2009140506 A1 | 11/2009 |
| WO | WO2010036980 A1 | 4/2010 |
| WO | WO2010039967 A1 | 4/2010 |
| WO | WO2012112378 A2 | 8/2012 |
| WO | WO2013009881 A2 | 1/2013 |

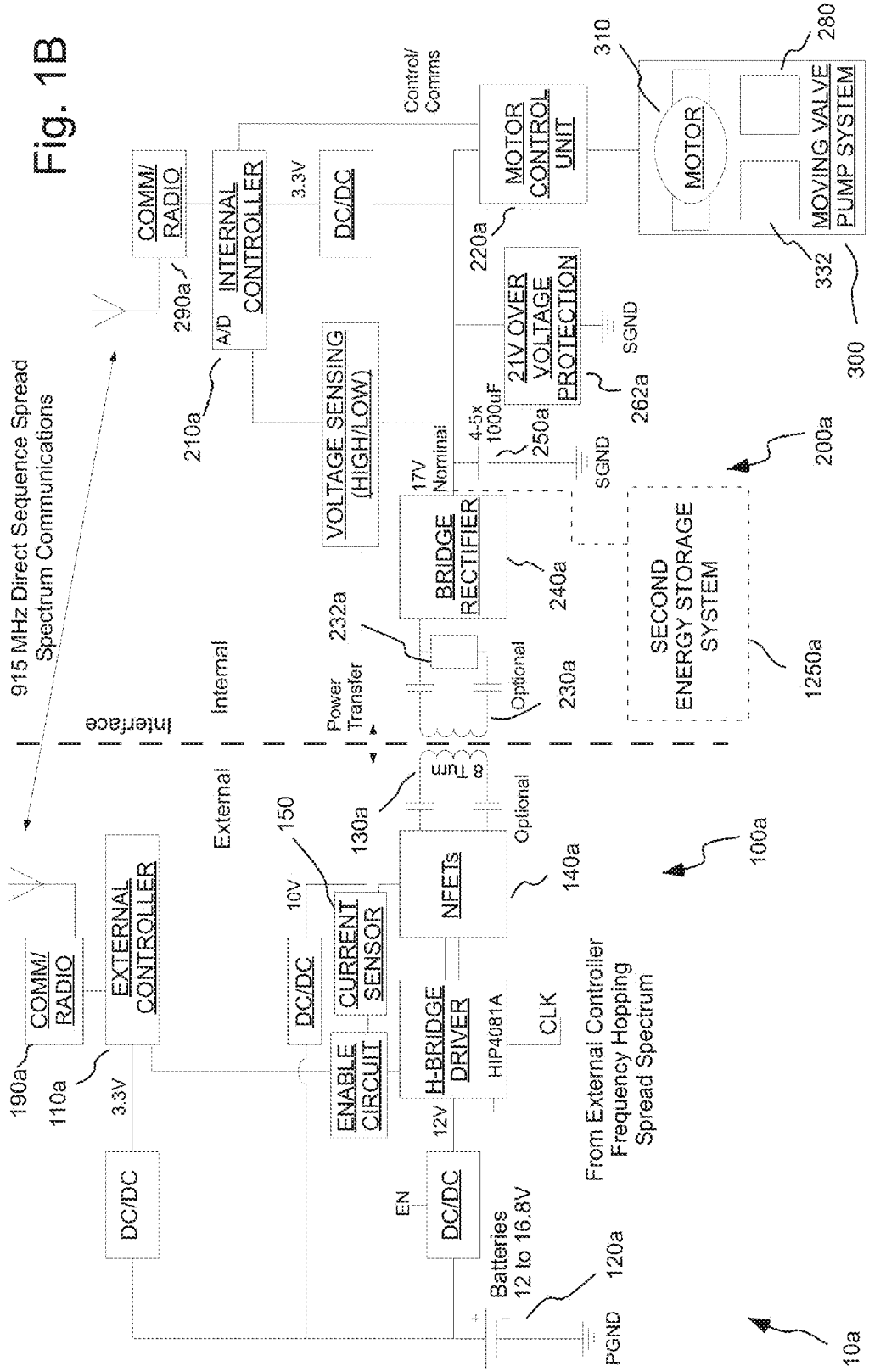

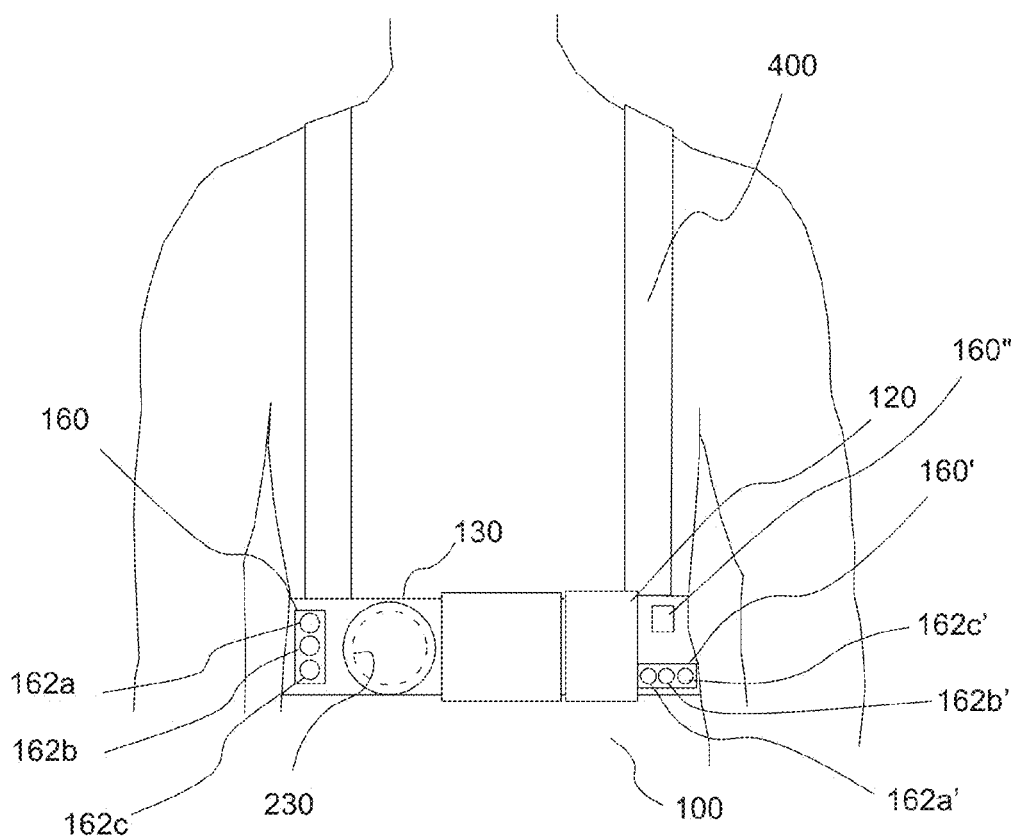

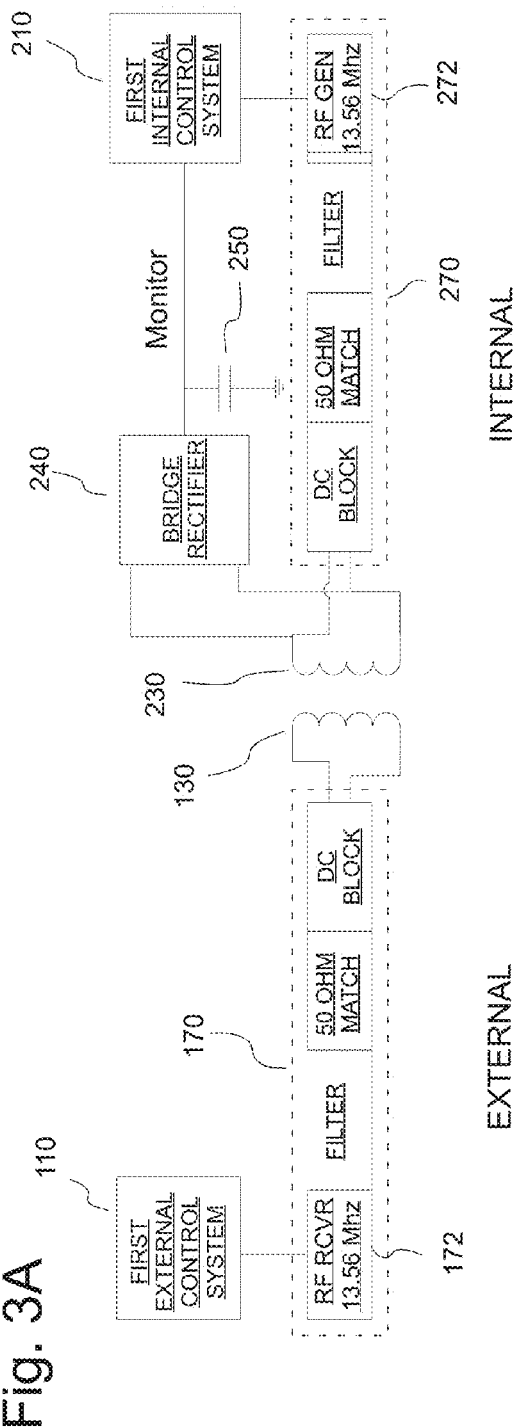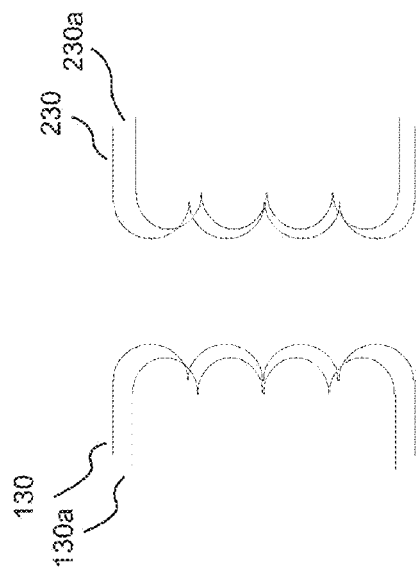

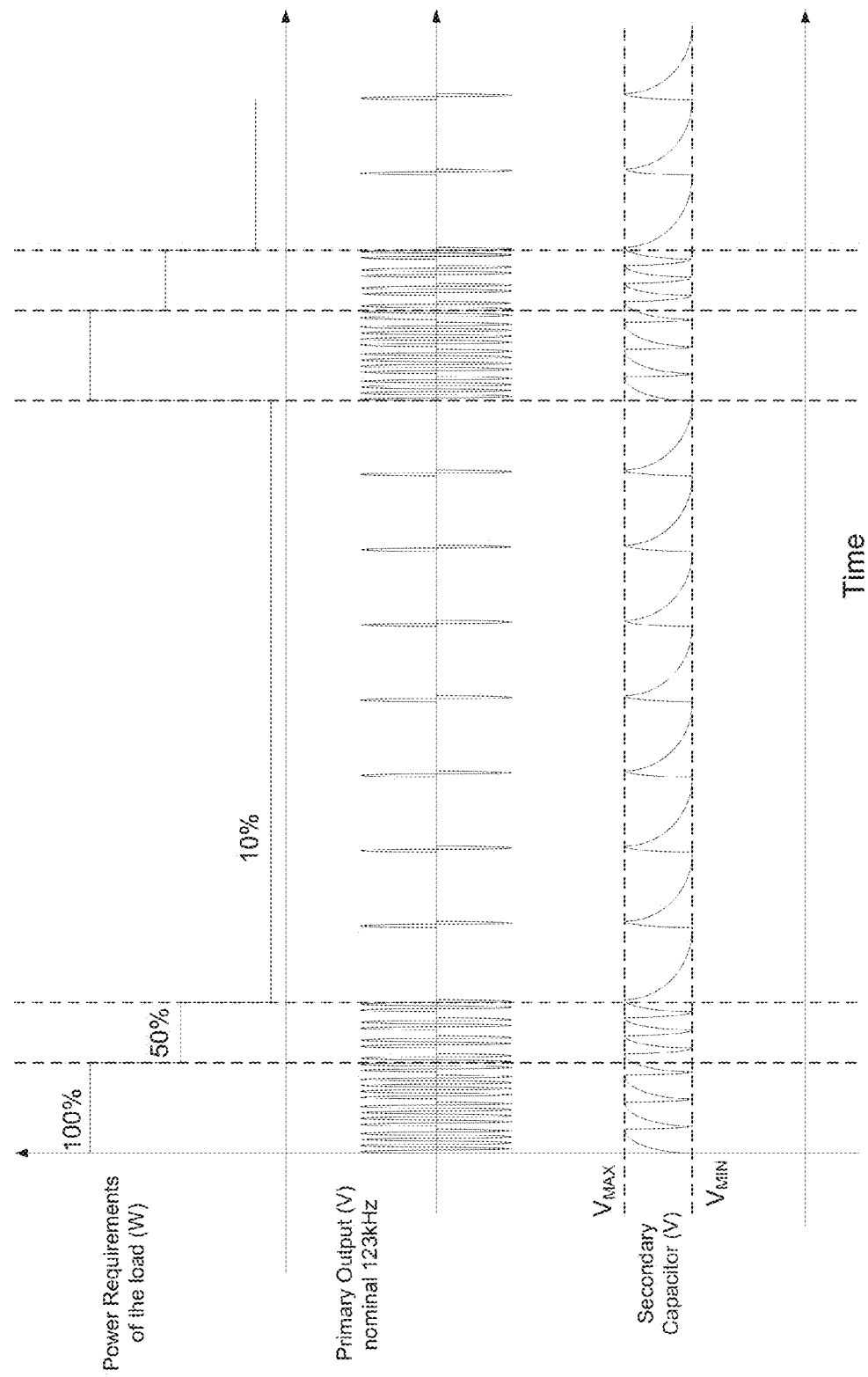

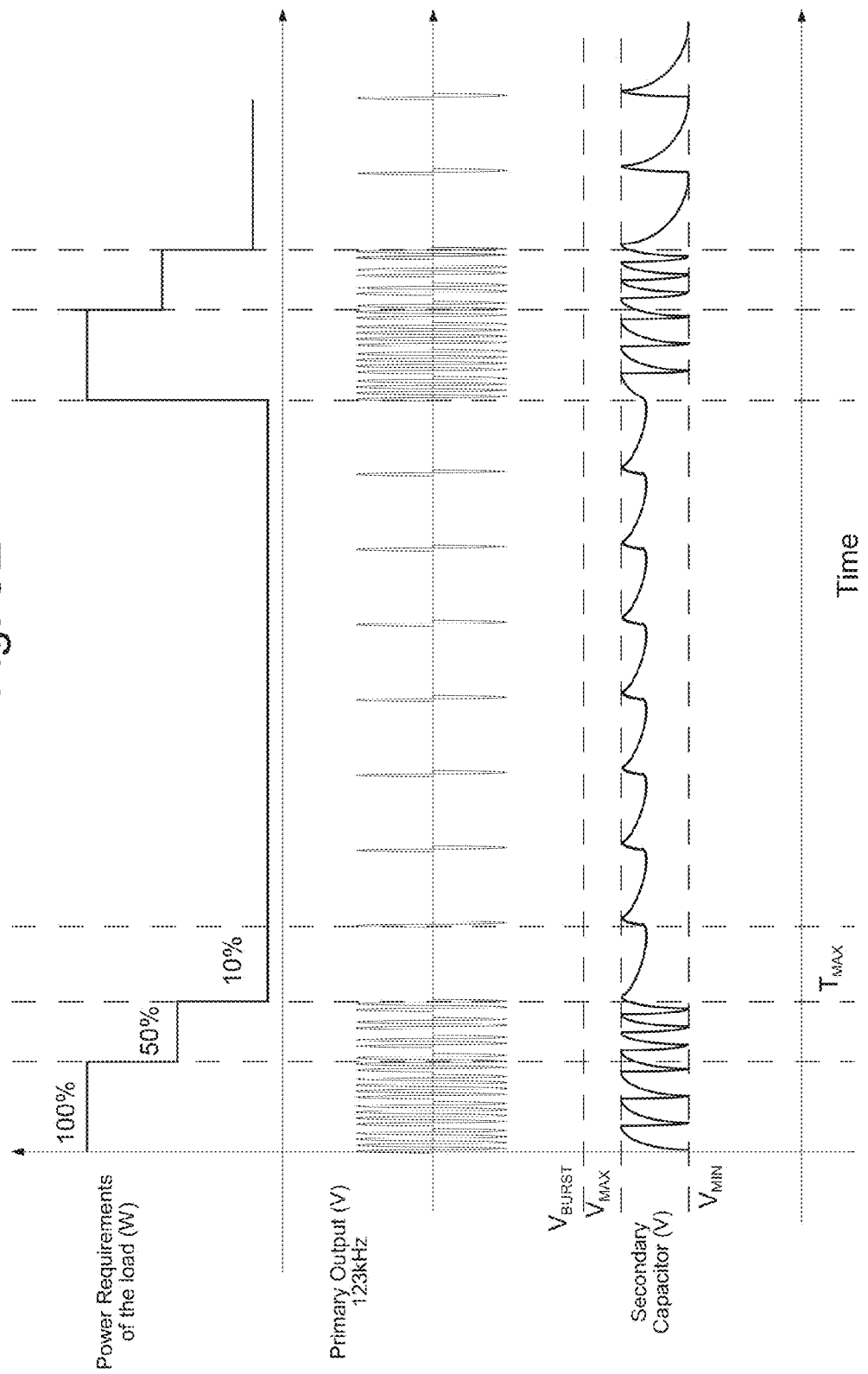

TRANSCUTANEOUS POWER TRANSMISSION AND COMMUNICATION FOR IMPLANTED HEART ASSIST AND OTHER DEVICES

CROSS REFERENCE TO RELATED APPLICATION

This application claims benefit of U.S. Patent Application Ser. No. 61/506,621, filed Jul. 11, 2011, the disclosure of which is incorporated herein by reference.

BACKGROUND

The following information is provided to assist the reader to understand the technology described below and certain environments in which such technology can be used. The terms used herein are not intended to be limited to any particular narrow interpretation unless clearly stated otherwise in this document. References set forth herein may facilitate understanding of the technology or the background thereof. The disclosure of all references cited herein are incorporated by reference.

Increasingly, medical devices are being implanted within patients to, for example, treat and/or diagnose various conditions. Implanted medical devices can be used to improve the quality of life as well as to prolong or save lives. Applications for implanted medical devices include, but are not limited to, regulating heart rates, assisting in blood flow, controlling incontinence, helping in hearing, helping to restore control of paralyzed organs and treating depression.

As used herein, the term "powered" refers generally to electrically powered medical devices. As used herein, the term "implanted" refers to a medical device either partially or completely inserted into the body of a patient (for example, a human patient). Often, the implanted medical device is completely or fully inserted into the body. In a number of such devices in which power must be supplied from an external source, power is delivered to the device and/or communications are maintained with the device via percutaneous wires that connect one or more external systems with the implanted device.

Heart assist or blood flow assist devices have been fully implanted within patients to assist the heart in providing adequate blood flow for the needs of the body. Typically, the normal heart provides 1.5 average watts of useful power, which equates to 1.5 joules per second of useful blood work, to satisfy the body's metabolic needs. A severely impaired heart might provide half this power and a heart assist device may make up the difference by providing, for example 0.75 watts of useful power. If the assist device is 15% efficient, it will require a minimum of 5 watts of input power. Heart assist devices in clinical use today use wires that pierce the skin to provide power for the fully implanted assist device. However, use of such percutaneous wires results is a significant risk of infection along the wire track.

In a number of other implanted medical devices in which power must be provided from an external source, a transcutaneous energy transfer system (TETS) is used to wirelessly provide power to the implanted medical device. In a number of such systems, a secondary power coil is implanted and is electrically connected to an implanted rechargeable battery which powers the implanted medical device. A system controller including a primary power coil and a battery is worn by the patient outside of the body. The primary coil transmits energy/power via magnetic force/induction from the external battery across the skin of patient to the secondary coil without requiring piercing of the skin. The external battery can, for example, be removable and rechargeable. Typically, transcutaneous energy transfer systems are used for energy transmission in relatively low power applications (for example, less than 1 watt).

Although it is desirable to develop transcutaneous energy transfer systems for use with implanted heart assist devices to, for example, obviate the risk associated with percutaneous wiring, a number of significant problems persist. As described above, the power requirements for implanted heart assist devices are substantially higher than with many other medical devices, complicating the use of transcutaneous energy transfer systems. Moreover, in the case of continuous flow heart assist devices, loss of power carries a risk of death of up to 40%. A number of precautions, including, for example, use of a plurality of redundant external battery packs, may be required for safety.

SUMMARY

In one aspect, a system includes an implantable pump system for assisting blood flow in a patient including at least one movable valve. The movable valve is in a normally open state when the moveable valve is not being powered and a drive system in operative connection with the moveable valve to move the moveable valve under power. The system further includes an energy transfer system to provide energy to the drive system. The energy transfer system includes an external system including a power source and an external coil and an internal system including an internal coil adapted to receive transcutaneous energy transmitted from the external coil. The internal system has at least a first state wherein energy transmission from the external coil is required to provide operational power to the drive system. The internal system may, for example, be inoperable to power the drive system to move the moveable pump through one stroke without energy transmission from the external coil when the internal system is in the first state.

The internal system may, for example, include a first energy storage device in electrical connection with the internal coil and the drive system. Energy is provided to the drive system via the first energy storage system. In a number of embodiments, the first energy storage system includes no battery. The first energy storage system may, for example, include a capacitor system (which, for example, includes one or more capacitors). In a number of embodiments, the first energy storage is capable of storing no more than 260 Joules (J) of energy, no more than 130 J, 13 J, 6.5 J or even 1 J.

The external system may, for example, include an external control system in operative connection with the power source and the external coil. The internal system may, for example, include an internal control system in operative connection with the first energy storage system and the internal coil. The external system may further include an external communication system in operative connection with the external control system. The internal system may further include an internal communication system in operative connection with the internal control system.

In a number of embodiments, the internal communication system is adapted to wirelessly transmit a signal to the external communication system to provide information related to a voltage of the first energy storage system. The external system may, for example, be adapted to cause the power source to energize the external coil upon receiving information transmitted from the internal communication system indicating that the voltage is at least as low as a lower threshold value to charge the first energy storage system and to de-energize the external coil upon receiving information transmitted from the internal communication system indicating that the voltage is at least as high as a higher threshold value.

In a number of embodiments, the external control system is adapted to cause the power source to energize the external coil after a determined maximum time period that the external coil has not been energized regardless of whether or not the voltage is at least as low the lower threshold value. The external control system may, for example, be adapted to cause the power source to energize the external coil in a manner to result in the voltage being greater than the higher threshold value in anticipation of a required high energy load.

In a number of embodiments, when the external coil is energized, energy is transmitted from the external coil to the internal coil over a range of frequencies. Energy may, for example, be transmitted from the external coil to the internal coil in a range of frequencies under control of a spread spectrum algorithm. The nominal transmission frequency may, for example, be between 50 and 500 kHz. In a number of embodiments, the range of frequencies extends from approximately 120 kHz to approximately 130 kHz. In a number of embodiments, the range of frequencies extends from approximately 120 kHz to approximately 126 kHz.

The external system and the internal system may, for example, be adapted such that a change of frequency of energy transmitted from the external coil to the internal coil of +/−10% results in a change in transfer efficiency of no greater than 10%. The external system and the internal system may, for example, be adapted to operate as a band-pass filter. In a number of embodiments, tuning capacitors and leakage inductances form series elements of the band-pass filter and magnetizing inductance forms a shunt element. Fixed tuning capacitors may, for example, be used. The resonant frequency of at least one of the internal coil or the external coil may also be tunable. In a number of embodiments, the system has a Q factor less than 10.

The spread spectrum algorithm may, for example, be a frequency hopping spread spectrum algorithm. The spread spectrum algorithm may also be a direct sequence spread spectrum algorithm. In a number of embodiments, energy is transmitted from the external coil to the internal coil in the range of frequencies with a set resonant frequency of the external coil and a set resonant frequency of the internal coil.

In a number of embodiments wherein the external system includes an external communication system and the internal system includes and internal communication system, the external communication is adapted to transmit to or receive informational signals from the internal communication system via at least one of an external radio or the external coil, and the internal communication system is adapted to transmit information signals to or receive signals from the external communication system via at least one of an internal radio or the internal coil. Information signals may, for example, be transmitted between the external coil and the internal coil within a frequency range different from a frequency range at which energy is transmitted from the external coil to the internal coil.

In a number of embodiments wherein the external system includes an external communication system and the internal system includes and internal communication system, the internal communication system may, for example, be adapted to transmit a periodic status signal to confirm operability of at least a portion of the internal system.

The system may further include a monitoring system to measure a variable related to current draw by the external coil to provide information to the patient regarding position of the external coil relative to the internal coil based at least in part on the measured variable related to current draw on the external coil. The monitoring system may, for example, include a current sensor in electrical connection with the external coil and in communicative connection with the external control system.

In a number of embodiments, the internal system further includes a second energy storage system. The internal system may have a second state wherein energy is drawn from the second energy storage system to provide energy to the drive system. In a number of embodiments, the second energy storage system stores sufficient energy to provide operation power to the drive system without transfer of energy from the external coil. The second energy storage system may, for example, include an internal rechargeable battery. In a number of embodiments, the internal system may be placed in the second state upon instructional information being transmitted from the external control system via the external communication system to the internal control system via the internal communication system. The external system may, for example, be adapted to allow the patient to manually cause the internal system to be in the second state. In a number of embodiments, no energy is drawn from the second energy storage system (for example, a rechargeable battery) to provide energy to the drive system in the first state. The second energy storage system (for example, a rechargeable battery) may, for example, be adapted to power (or to provide operation power to) the drive system for a period of time in the range of 5 minutes to 2 hours.

In a number of embodiments, the power source of the external system consists of a single rechargeable battery pack. The battery pack may, for example, include a plurality of lithium ion battery cells.

In a number of embodiments, the external coil is energized at a voltage of sufficient amplitude to provide an efficiency of at least 75%.

In a number of embodiments, the systems described above may, for example, be used in connection with implanted blood flow assist systems other than those including moveable valve pump systems and also with implanted systems/devices other than blood flow (heart) assist systems. In that regard, in another aspect, a system includes an implantable device and an energy transfer system to provide energy to the drive system. The energy transfer system includes an external system including a power source and an external coil. The energy transfer system further includes an internal system including an internal coil adapted to receive transcutaneous energy transmitted from the external coil. The internal system has at least a first state wherein energy transmission from the external coil is required to provide operational power to the implanted device (for example, to the drive system of an implanted blood flow assist device). As described above, the internal system may further include a second energy storage system. The internal system may have a second state wherein energy is drawn from the second energy storage system to provide energy to the implanted device. In a number of embodiments, the second energy storage system stores sufficient energy to provide operation power to the implanted device without transfer of energy from the external coil. The second energy storage system may, for example, include an internal rechargeable battery. In a number of embodiments, the internal system may be placed in the second state upon instructional information being transmitted from the external control system via the external communication system to the internal control system via the internal communication system. The external system may, for example, be adapted to allow the patient to manually cause the internal system to be in the second state. In a number of embodiments, no energy is drawn from the second energy storage system (for example, a rechargeable battery) in the first state. The second energy storage system (for example, a rechargeable battery) may, for example, be adapted to power (or to provide operation power to) the implanted device for a period of time in the range of 5 minutes to 2 hours (without receiving energy from the external coil).

In another aspect, an energy transfer system includes a first system including a power source, a first control system, and a first coil in operative connection with the first control system. The system further includes a second system including a second coil adapted to receive wireless energy transmitted from the first coil. When the first coil is energized, energy is wirelessly transmitted from the first coil to the second coil over a range of frequencies under control of a spread spectrum algorithm. The spread spectrum algorithm may, for example, be a frequency hopping spread spectrum algorithm. The spread spectrum algorithm may, for example, be a direct sequence spread spectrum algorithm. In a number of embodiments, the system has a Q factor less than 10.

In a number of embodiments, the first system and the second system are adapted such that a change of frequency of energy transmitted from the first coil to the second coil of +/−10% results in a change in transfer efficiency of no greater than 10%. The first system and the second system may, for example, be adapted to operate as a band-pass filter. Tuning capacitors and leakage inductances may, for example, form series elements of the band-pass filter and magnetizing inductance may, for example, forms a shunt element.

The system may for example, include fixed tuning capacitors. The resonant frequency of at least one of the internal coil or the external coil may, for example, be tunable. Energy may, for example, be transmitted from the external coil to the internal coil in the range of frequencies with a set resonant frequency of the external coil and a set resonant frequency of the internal coil.

In a number of embodiments, the first coil is an external coil adapted to be outside of a body and the second coil is an internal coil adapted to be implanted within a body. The first coil is adapted to transcutaneously transmit energy to the second coil.

In a number of embodiments, the external coil is energized at a voltage of sufficient amplitude to provide an efficiency of at least 75%.

In a further aspect, a method of assisting blood flow in a patient includes: placing an implantable pump system in fluid connection with a blood vessel, the implantable pump system including at least one movable valve, the movable valve being in a normally open state when the moveable valve is not being powered, a drive system in operative connection with the moveable valve to move the moveable valve under power; providing an external system including a power source and an external coil; providing an internal system including an internal coil adapted to receive transcutaneous energy transmitted from the external coil; and operating the internal system in a first state wherein energy transmission from the external coil is required to provide operational power to the drive system. Closing of the valve may also occur under power in a forward stroke of the valve.

In another aspect, a method of powering a device includes: providing a first system including a power source, a first control system, and a first coil in operative connection with the first control system; providing a second system including a second coil adapted to receive wireless energy transmitted from the first coil, and wirelessly transmitting energy from the first coil to the second coil over a range of frequencies under control of the spread spectrum algorithm. In a number of embodiments wherein the first coil is an external coil placed outside of a body and the second coil is an internal coil implanted within a body, the first coil is adapted to transcutaneously transmit energy to the second coil.

In another aspect, a system for use in connection with an implantable device includes an external system including a power source, an external coil and an external control system including a first external controller and a first external communication system in operative connection with the first external controller and with the external coil. The system further includes an internal system including an internal coil adapted to receive transcutaneous energy transmitted from the external coil, an energy storage system such as a capacitor system including at least one capacitor in electrical connection with the internal coil and adapted to be placed in electrical connection with the implantable device to provide energy to the implantable device, and an internal control system including a first internal controller and a first internal communication system in operative connection with the first internal controller and with the internal coil. The first internal communication system is adapted to wirelessly transmit a signal to the first external communication system to provide information related to a voltage of the capacitor system. The first external controller is adapted to energize the external coil upon receiving information transmitted from the first internal communication system that the voltage is at a lower threshold value to charge the capacitor system and to de-energize the external coil upon receiving information transmitted from the first internal communication system that the voltage is at a higher threshold value.

In a number of embodiments, the energy storage system/capacitor system does not store sufficient energy to power the implantable device for more than one second without energizing (in real time) the first coil. In a number of embodiments, the external coil may be energized at a voltage of sufficient amplitude to provide an efficiency of at least 75% or an efficiency of at least 80%.

When the external coil is energized, energy may, for example, be transmitted from the external coil to the internal coil over a range of frequencies. Energy may, for example, be transmitted from the external coil to the internal coil in a range of frequencies via a spread spectrum signal. In a number of embodiments, the range of frequencies extends from approximately 120 kHz to approximately 130 kHz or from approximately 120 kHz to approximately 126 kHz.

The external system and the internal system may, for example, be adapted such that a change of frequency of energy transmitted from the first coil to the second coil of +/−10% results in a change in transfer efficiency of no greater than 10%. The external system and the internal system may, for example, be adapted to operate as a band-pass filter. Tuning capacitors and leakage inductances form series elements of the band-pass filter and magnetizing inductance may, for example, form a shunt element.

In a number of embodiments, the first internal communication system is adapted to transmit information including information related to the voltage of the capacitor system via the internal coil and the external coil at a frequency outside of the range frequencies at which the external coil transmits energy to the internal coil and independently of transmission of energy from the external coil to the internal coil.

The first internal communication system may also be adapted to transmit a periodic supervisory signal or status signal to confirm operability of at least a portion of the internal control system. The first internal communication system may, for example, include a radio frequency transmitter to transmit information, and the first external communication system may, for example, include a radio frequency receiver to receive information from the radio frequency transmitter. In a number of embodiments, the radio frequency transmitter transmits at a frequency of approximately 13.56 MHz and the radio frequency identification receiver receives at a frequency of approximately 13.56 MHz.

In a number of embodiments, the system further includes a system to measure a variable related to current draw by the external coil and a system to provide information to the patient regarding position of the external coil relative to the internal coil based at least in part on the measured variable related to current draw on the external coil. The system to measure a variable related to current draw on the external coil may, for example, include a current sensor in electrical connection with the external coil and in communicative connection with the first external controller.

In a number of embodiments, the internal control system further includes a second internal communication system, and the external control system further includes a second external communication system. The second internal communication system may, for example, be adapted to communicate wirelessly and bi-directionally with the second external communication system independently of the internal coil and the external coil. The second internal communication system may, for example, communicate with the second external communication system via radio frequency energy of a different frequency from which the first internal communication system communicates with the second external communication system. The frequency at which the second internal communication system communicates with the second external communication system may, for example, be in the range of approximately 402 MHz to approximately 405 MHz.

In a number of embodiments, the internal control system further includes a second internal controller in operative connection with the implanted device and in communicative connection with the second internal communication system. At least one of the second internal communication system and the second external control system may, for example, be adapted to communicate bi-directionally with another external communication system. In a number of embodiments, the another external communication system is adapted to provide information to a person other than the patient regarding at least one operational parameter of the implanted device or at least one patient physiological parameter. The internal control system may, for example, be adapted to be programmed by the person other than the patient to alter operation of the implanted device via communication from the another external communication system.

In another aspect, a method for operating a device implanted in a patient includes: positioning an external system including an external coil and an external control system comprising a first external controller and a first external communication system in operative connection with the first external controller adjacent the patient; implanting within the patient an internal system including an internal coil adapted to receive transcutaneous energy transmitted from the external coil, an internal energy storage system such as a capacitor system including at least one capacitor in electrical connection with the internal coil and adapted to be placed in electrical connection with the implantable device to provide energy to the implantable device, and an internal control system including a first internal controller and a first internal communication system in operative connection with the first internal controller and with the internal coil; wirelessly transmitting a signal from the first internal communication system to the first external communication system to provide information related to a voltage of the capacitor system; energizing the external primary coil upon receiving information transmitted from the first internal communication system that the voltage is at a lower threshold value to charge the at least one capacitor; and de-energizing the external primary coil upon receiving information transmitted from the first internal communication system that the voltage is at a higher threshold value.

In another aspect, a system for use in connection with an implanted device includes an external system including a power source, an external control system, and an external coil in operative connection with the external control system; and an internal system including an internal coil adapted to receive transcutaneous energy transmitted from the external coil, wherein, when the external coil is energized, energy is transcutaneously transmitted to from the external coil to the internal coil over a range of frequencies via a spread spectrum signal.

In a further aspect, a method of powering an implanted device includes: providing an external system including a power source, an external control system, and an external coil in operative connection with the external control system; providing an internal system including an internal coil in connection with the implanted device and adapted to receive transcutaneous energy transmitted from the external coil, and energizing the external coil so that energy is transmitted from the external coil to the internal coil transcutaneously over a range of frequencies via a spread spectrum signal.

In another aspect, a system for use in connection with an implantable device includes an external system including a power source, an external coil and an external control system including a first external controller and a first external communication system in operative connection with the first external controller and with the external coil. The system further includes an internal system including an internal coil adapted to receive transcutaneous energy transmitted from the external coil, a first energy storage system such as a capacitor system including at least one capacitor in electrical connection with the internal coil and adapted to be placed in electrical connection with the implantable device to provide energy to the implantable device, and an internal control system including a first internal controller and a first internal communication system in operative connection with the first internal controller and with the internal coil. The first internal communication system is adapted to wirelessly transmit a signal to the first external communication system to provide information related to a voltage of the capacitor system. The first external controller is adapted to energize the external coil upon receiving information transmitted from the first internal communication system that the voltage is at a lower threshold value to transfer power from the external coil to the internal coil charge the capacitor system and to de-energize the external coil upon receiving information transmitted from the first internal communication system that the voltage is at a higher threshold value. The first internal communication system is further adapted to transmit a periodic supervisory or status signal via, for example, the internal coils and the external coil to confirm operability of the internal control system.

The system may further include a system to measure a variable related to current draw on the external coil. The system to measure a variable related to current draw on the external coil may, for example, include a current sensor in electrical connection with the external coil and in communicative connection with the first external controller.

In a number of embodiments, during initiation of power transfer from the external coil to the internal coil, the external control system is adapted to energize the external coil for a first period of time and monitor for a signal from the internal system for a second period of time. In a number of embodiments, the signal from the internal system is one of a signal transmitting information from the first internal communication system that the voltage is at the lower threshold value, a signal transmitting information from the first internal communication system that the voltage is at the higher threshold value, or the periodic supervisory signal. The external control system may, for example, be adapted to de-energize the external coil if no signal is received within the second period of time for a defined delay period and energize the external coil after the delay period. In a number of embodiments, the first external controller is adapted to de-energize the external coil when the variable related to current draw on the external coil reaches a threshold value and re-energize the external coil to initiate power transfer at a later time.

In another aspect, a system for use in connection with an implantable device includes an external system including a power source, an external coil and an external control system including a system to measure a variable related to current draw on the external coil. The system further includes an internal system including an internal coil adapted to receive transcutaneous energy transmitted from the external coil. The external control system is adapted to de-energize the external coil upon when the variable related to current draw on the external coil reaches a threshold value.

In a further aspect, a system for use in connection with an implantable device includes an external system including a power source, an external coil and an external control system including a first external controller and a first external communication system in operative connection with the first external controller and with the external coil. The system further includes an internal system including an internal coil adapted to receive transcutaneous energy transmitted from the external coil to provide energy to the implantable device, and an internal control system including a first internal controller and a first internal communication system in operative connection with the first internal controller and with the internal coil. The first internal communication system is adapted to transmit information to the first external communication to control energizing of the external coil independently of and at a different frequency than a frequency at which the external coil is energized to transmit power to the internal coil.

In a further aspect, a system or energy transfer system includes a first system including a power source, a first coil, and a first control system. The first control system includes a first controller and a first communication system. The first communication system is in operative connection with the first controller. The energy transfer system further includes a second system adapted to be placed in electrical connection with a load and including a second coil, at least one energy storage device, and a second control system. The second control system includes a second controller and a second communication system. The second communication system is in operative connection with the second controller. The first system is adapted to wirelessly transfer energy via the first coil to the second coil of the second system to, for example, provide energy to the load. The second communication system is adapted to transmit a signal to the first communication system via the second coil to the first coil to provide information related to a voltage level of the at least one energy storage device. The first controller is adapted to energize the first coil upon receiving information transmitted from the second communication system that the voltage level is at a lower threshold value to charge the at least one energy storage device. The first controller is also adapted to de-energize the first coil upon receiving information transmitted from the second communication system that the voltage level is at a higher threshold value.

In a number of embodiments, the at least one energy storage device adapted to provide energy to the load while the first coil is de-energized. In a number of embodiments, the at least one energy storage device does not contain sufficient energy to provide operational power to the load or to power the load for more than 20 seconds (or even one second) without transmission of energy from the first system.

In a number of embodiments, the external coil is energized at a voltage of sufficient amplitude to provide an efficiency of at least 75% or to provide an efficiency of at least 80%.

In a number of embodiments, the first system and the second system are adapted such that a change of frequency of energy transmitted from the first coil to the second coil of +/−10% results in a change in transfer efficiency of no greater than 10%. The first system and the second system may, for example, be adapted to operate as a band-pass filter. In a number of embodiments, tuning capacitors and leakage inductances form series elements of the band-pass filter and magnetizing inductance forms a shunt element. In an number of embodiments, when the first coil is energized, energy is transmitted from the first coil to the second coil over a range of frequencies via a spread spectrum signal.

At least the second system may be internal to a body.

Energizing and de-energizing or on/off cycling of the first coil may, for example, be effected by On-Off keying or On-Off modulating the power transmission frequency, enabling-disabling a primary driver for the first coil or enabling-disabling an H-bridge driver for the first coil.

In still a further aspect, an energy transfer system includes a first system including a power source, a first control system, and a first coil in operative connection with the first control system; and a second system including a second coil adapted to receive wireless energy transmitted from the first coil. When the first coil is energized, energy is wirelessly transmitted from the first coil to the second coil covering a range of frequencies and produced by a spread spectrum signal. The spread spectrum signal may, for example, be frequency hopping spread spectrum. The spread spectrum signal may, for example, be direct sequence spread spectrum. In a number of embodiments, the system has a Q factor less than 10.

The first system and the second system may, for example, be adapted such that a change of frequency of energy transmitted from the first coil to the second coil of +/−10% results in a change in transfer efficiency of no greater than 10%. In a number of embodiments, the first system and the second system are adapted to operate as a band-pass filter. In a number of embodiments, tuning capacitors and leakage inductances form series elements of the band-pass filter and magnetizing inductance forms a shunt element.

The resonant frequency or the center frequency need not be changed in effecting the spread spectrum signal. The system may thus include fixed tuning capacitors.

In a number of embodiments hereof, a fully implanted moving valve heart assist system derives its operational power in real time, during a first operational state, from an external power source (for example, via TETS). The external power source may, for example, be provided by a non-redundant single source (for example, a single battery back). In a number of embodiments, the system also includes an implanted rechargeable battery capable of operationally powering the moving valve heart assist device for a period of time when the system is in a second operational state, thereby temporarily eliminating TETS related electromagnetic emissions and/or temporarily eliminating the need for externally supplied TETS power.

The technology described herein, along with the attributes and attendant advantages thereof, will best be appreciated and understood in view of the following detailed description taken in conjunction with the accompanying drawings.

BRIEF DESCRIPTION OF THE DRAWINGS

FIG. 1B illustrates another embodiment of a system hereof for transcutaneous energy and data transmission.

FIG. 2 illustrates a wearable article (for example, a vest) on a patient to support and position an external system such as the system of FIG. 1A or 1B.

FIG. 3A illustrates a power control system of the system of FIG. 1A.

FIG. 3B illustrates an embodiment of a system in which data communication coils are positioned within the volume of power transfer coils.

FIG. 5B illustrates power requirements of the load (implanted device), external/primary AC output voltage and voltage of the internal/secondary capacitor system as a function of time.

FIG. 5E illustrates power requirements of the load (implanted device), external/primary AC output voltage and voltage of the internal/secondary capacitor system as a function of time.

DETAILED DESCRIPTION

As used herein and in the appended claims, the singular forms "a," "an", and "the" include plural references unless the content clearly indicates otherwise. Thus, for example, reference to "a capacitor" includes a plurality of such capacitors and equivalents thereof known to those skilled in the art, and so forth, and reference to "the capacitor" is a reference to one or more such capacitors and equivalents thereof known to those skilled in the art, and so forth. Indication herein that one element, system or component is in connection with another element, system or component (for example, operative connection, electrical connection, communicative connection etc.) includes either direct connection or indirect connection (for example, via one or more intermediary elements or components) unless the content clearly indicates otherwise.

In a number of representative embodiments hereof, a high-power energy and information transfer or communication system is used to power and bi-directionally communicate control and status information wirelessly (for example, transcutaneously or otherwise through body volume/mass) with one or more implanted medical devices. The system, for example, transfers power transcutaneously by electromagnetic induction from an externally worn battery pack to the implanted device without the need for percutaneous leads. In that regard, an external coil inductively couples power to an internal coil implanted beneath the skin. The energy and information transfer or communication systems hereof can also be used in connection with devices or systems other than implanted medical devices to wirelessly transfer energy.

Figure 1A:
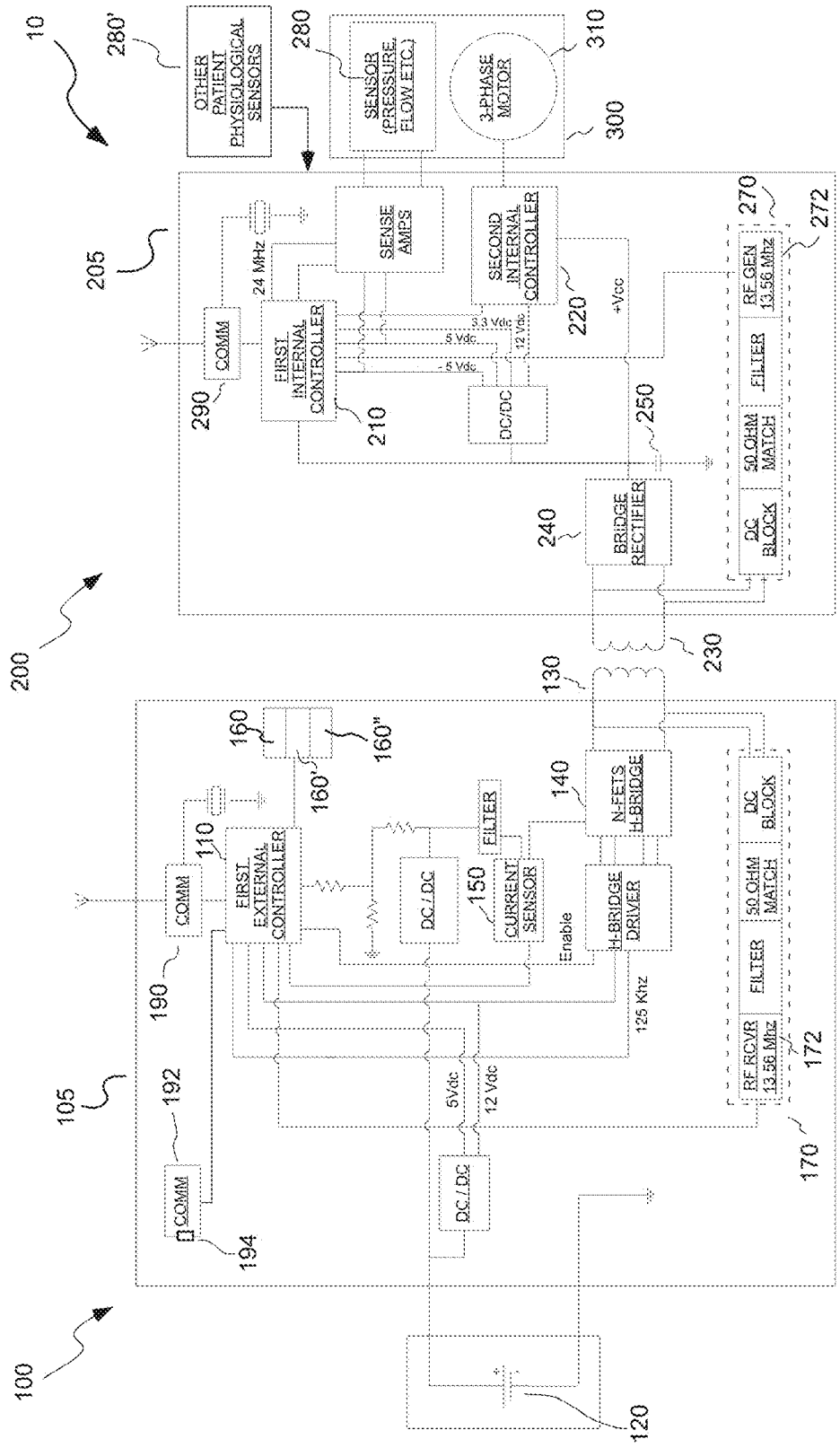
FIG. 1A illustrates an embodiment of a system hereof for transcutaneous energy and data transmission.

In a number of embodiments, a system 10 as illustrated in FIG. 1A may, for example, be described as (at least in part) an inductively coupled DC-DC convertor. In FIG. 1A, a primary or external system 100 of system 10 includes an external control system 105 including at least a first external controller 110 (for example, a micro-controller or microprocessor). External system 100 further includes an external power source 120 (for example, a single rechargeable battery pack), and an external coil 130 (often referred to as a primary coil). Coil power driver circuitry in electrical connection with external coil 130 can, for example, include an H-bridge inverter 140 to which control and timing signals are provided by first external controller 110 (including, for example, control of pulse width modulation (PWM) duty cycle and/or switching frequency). Secondary, internal or implanted system 200 includes, for example, an implanted or internal coil 230 (often referred to as a secondary coil) and a control system 205 including one or more controllers, a rectifier 240, and power conditioning circuitry.

In the illustrated embodiment, internal control system 205 includes a first internal controller 210, (for example, microcontroller or processor) which is adapted to, for example, control certain "housekeeping" control processes as further described below. Internal control system 205 further includes a second internal controller 220 to, for example, control an implanted device 300. The functions of first and second controllers 210 and 220 can, for example, be combined in a single control system or distributed over more than two controllers.

In a number of embodiments, implanted device 300 is an implanted blood flow assist pump including a motor 310 as, for example, described in U.S. patent application Ser. Nos. 13/370,113, 13/370,137 and 13/370,155 and PCT International Patent Application No. PCT/US2012/024572, the disclosures of which are incorporated herein by reference. One skilled in the art appreciates, however, that system 10 can be used in connection with any implantable device for which power from an external system is to be provided.

In a number of embodiments, system 10 compensates for coil alignment and coupling variations between external coil 130 and internal coil 230 by detecting and adjusting for changes in the system resonant frequency or coupling efficiency. In a number of representative embodiments, which were not optimized, the system is able to deliver maximum output power of approximately 35 watts at a coil separation or translational misalignment of up to 25 mm and rotational misalignment of 30 degrees, and operates at a maximum efficiency of, for example, 75%, 80% or higher. Components of external system 100 can, for example, be supported by or carried within a wearable article 400 such as a vest (see FIG. 2) that can also operate to align external coil 130 with internal coil 230. It is, for example, desirable to minimize orientational misalignment and to minimize a separation gap or distance between external coil 130 and internal coil 230. In that regard, increasing misalignment and/or increasing separation reduces coil coupling/power transfer efficiency. Many currently available transcutaneous energy transfer systems are quite sensitive to coil coupling effects caused by changes in alignment and/or separation. Alignment and/or separation problems may, for example, result from normal patient movement, and the system must accommodate patient-to-patient variations such as skin thickness and tension.

In general, changes in coil coupling result in changes in the resonant frequency of the transcutaneous energy transfer system transformer or result in system coupling losses, which can reduce power transfer and efficiency. In a number of embodiments, system 10 was designed to address the problem of changes in coil coupling by, for example, sensing a variable related to or dependent upon current draw, which increases with misalignment, on external coil 130 (for example, via a current sensor 150 in electrical connection with coil 130). A system to provide information regarding the state of coil coupling to the patient may, for example, be provided. For example, an indicator system 160 can be provided on article 400 to notify the patient of alignment and/or separation problems. Indicator system 160 may, for example, provide information to the patient in one or more manners adapted to be sensed by the patient (for example, audibly, visually, and/or tactilely). Indicator system 160 may, for example, include a series of visual indicators 162a, 162b, 162c etc. (for example, red, yellow, and green indicator lights) on article 400. Another indicator system 160' can, for example, provide information to the patient regarding the charge status of battery pack 120 in a manner adapted to be sensed by the patient (for example, audibly, visually, and/or tactilely). Indicator system 160' may, for example, include a series of visual indicators 162a', 162b', 162c' etc. (for example, red, yellow, and green indicator lights) on article 400.

Another problem to be addressed by transcutaneous energy transfer systems is variation in the power demanded by implanted device 300. In a number of embodiments hereof, compensation for variations in the electrical load (that is, the power demanded by implanted device 300) occurs through a control protocol or methodology implemented between external system 100 and internal system 200 in which external coil 130 is either energized (powered on) or de-energized (powered off) as a function of the power demanded. System 10 is designed to accommodate variations in load and power demand through a power control system, subsystem or circuitry (see, for example, FIG. 3A).

In a number of embodiments, internal system 200 has at least a first state or first operational state in which implanted device 300 cannot be operated in a typical, normal or clinically effective manner (that is, in a manner to achieve its intended purpose) without real-time transfer of energy from external coil 130. In that regard, energy transmission from external coil 130 is required in such embodiments to provide operational power to the implanted device. In a number of embodiments, no energy from an internal battery (that is, a device in which chemical energy is converted to electrical energy) is supplied to implanted device when internal system 200 is in the first state. In general, rechargeable batteries have limited recharge cycles (for example, several hundred to a thousand) and thus may have a relatively limited life compared to other energy storage systems. In a number of embodiments, an internal battery may be present in internal system 200, but it does not provide energy to implanted device 300 when internal system 200 is in the first state.

In the embodiment illustrated in, for example, FIGS. 1A and 3A, first internal controller 210 monitors a voltage or a variable related to or dependent upon the voltage on the output of implanted bridge rectifier 240, which corresponds to a voltage of a first internal energy storage system 250 which is charged via the system transformer. In a number of embodiments, first internal energy storage system 250 does not include a battery. Internal energy storage system 250 may, for example, include a capacitor system including one or more capacitors as, for example, illustrated in FIG. 1A. When discussing the embodiment of, for example, FIG. 1A, first internal energy storage system 250 may sometimes be referenced as capacitor system 250 herein. In a number of embodiments, the capacitance of capacitor system 250 is insufficient to provide operational power to implanted device 300 or is sufficient to hold enough energy to power the implanted device for a limited period of time (for example, in the range of approximately 10 milli-seconds to 1 second or any range therebetween). The stored energy may, for example, be sufficient to power implanted device 300 between bursts of energy from external/primary coil 130 but not sufficient to normally operate device 300 without the presence of external coil 130 supplying frequent bursts of energy In a number of representative embodiments for an implanted left ventricle or heart assist pump system as device 300, operational power or normal operation includes powering the pump motor for one complete functioning period, e.g. one stroke, one cycle, one rotation, etc. In a number of embodiments, first internal energy storage system 250 may, for example, store no more than approximately 260 Joule (J), 130 J, 13 J, 6.5 J or even 1 J.

As described above, a normal heart provides 1.5 watts of useful power to satisfy the body's metabolic needs. A severely impaired heart might provide half this power and a heart assist device may make up the difference by providing, for example 0.75 watts of useful power. In a number of embodiments, system 10 is adapted to provide at least 1 watt of power. In the case that implanted device 300 is a moving valve heart assist pump (sometimes referred to as a valve blood flow assist pump) as, for example, illustrated in FIG. 8 and discussed further below, pump system 300 operates, for example, when the native heart is contracting, or about 40% of the time. Given limitations in efficiency, a moving valve pump may require 5 to 35 (or even more) watts of power for assisting the failing heart.

Upon sensing that external coil 130 has been removed, implanted device 300 may gracefully shutdown. Capacitor system 250 or other first energy storage system 250 may, for example, operate in a manner similar to a filter capacitor, (that is, filtering a rectified spread spectrum signal (discussed below) and/or filtering the frequent bursts of energy from external coil 130 to provide a DC voltage to implanted device 300). In a number of embodiments, capacitor system 250 may, for example, have a capacitance to store sufficient energy to power some portion of internal system 200 while external coil 130 is de-energized or powered off to enable, for example, swapping a discharged battery 120 for a charged one. As an example, capacitor system 250 may hold enough energy to power implanted device 300 for several seconds while external battery 120 is replaced with a charged battery. During this time, implanted device 300 may switch to a low power mode to retain its memory and settings and may disable higher power functions such as, but not limited to, communications and/or powering a motor or pump of implanted device 300.

Upon the return of external coil 130, implanted device 300 will start to receive bursts of energy and may return to normal operation, including enabling any high power functions that were disabled. If after a predetermined time period or if after the voltage on capacitor system 250 reaches a minimum threshold voltage and implanted device 300 does not receive a burst of energy, internal system 200 or implanted device 300 may store any necessary information such as, but not limited to, settings, current memory, device state, or any other necessary information in nonvolatile memory for access and reconfiguration of implanted device 300 when power from external system 100 (via external coil 130) is restored.

When the measured voltage drops below a lower threshold (for example, nominally 12.5 VDC in a number of embodiments), first internal controller 210 causes a coded signal of that lower voltage state to be transmitted via an internal communication system including, for example, a first internal communication system or subsystem 270 to an external communication system including, for example, a first external communication system or subsystem 170. In a number of embodiments, the signal is transmitted via radio frequency energy between internal coil 230 and external coil 130. The signal may, for example, be transmitted at a different frequency from and independently of (for example, not overlayed or superimposed upon) the energy transmission signal between external coil 130 and internal coil 230. First external communication system 170 communicates with first external controller 110 which causes external coil 130 to be energized or powered on to transmit power from external battery pack 120 to capacitor system 250. When the measured voltage on the output of implanted bridge rectifier 240 rises to an upper threshold (for example, 16.5 VDC in a number of embodiments) first internal controller 210 causes a coded signal of that higher-voltage or charged state to be transmitted via first internal communication system 270 to first external communication system 170. Once again, the signal may be transmitted via radio frequency energy between internal coil 230 and external coil 130. Like the lower voltage signal, such a higher-voltage or "charged" signal may be transmitted by first internal communication system 270 at a different frequency from and independently of the energy transmission signal between external coil 130 and internal coil 230. First external communication system 170 communicates receipt of the high-voltage signal to first external controller 110 which causes external coil 130 to be de-energized or powered off. Under typical operating conditions, the measured internal voltage on the output of bridge rectifier will be a sawtooth waveform that averages approximately 14.5 VDC in the case that the lower threshold voltage is 12.5 VDC and the upper or higher threshold voltage is 16.5 VDC.

In a number of embodiments, the power control system is also adapted to provide a "watchdog", "supervisory" or "status" function. It is important for the external control electronics (including, for example, first external controller) to be able to determine that the internal power control system is functioning. For example, the absence of a lower voltage signal or a higher-voltage (charged) signal from the power control system to first external controller 110 during a period of acceptable internal operating voltage could be erroneously interpreted as an indication that the internal or implanted circuitry is no longer operational. To address such a failure risk, a coded "watchdog", "supervisory" or "status" signal may be periodically transmitted from the implanted electronics to the external electronics. The supervisory signal may, for example, be transmitted via radio frequency energy between internal coil 230 and external coil 130. Like the lower voltage signal and the higher-voltage signal, the supervisory signal may be transmitted by first internal communication system 270 at a different frequency from and independently of the energy transmission signal between external coil 130 and internal coil 230. First external communication system 170 communicates receipt of the supervisory signal to first external controller 110. The supervisory signal may, for example, be decoded by first external controller 110 and is used to reset a or supervisory timer. If the timer times out, first external controller 110 may, for example, notify the patient via one or more external indicators 160" (see FIG. 2) adapted to provide information to the patient of the supervisory time out in one or more manners adapted to be sensed by the patient (for example, audibly, visually, and/or tactilely). Receipt of a lower voltage or a higher-voltage signal can also reset the watchdog or supervisory timer. Therefore, in the above-discussed embodiment, three different coded signals or messages are communicated from the implanted power control system to the first external controller 110: "lower voltage", "higher voltage" or "charged" and "reset supervisory timer". The absence of the supervisory signal can also be used in conjunction with the current sensing capability of first external controller 110 to further improve the reliability of misaligned coil detection as described above.

In a number of embodiments, if the supervisory signal is not received in a predetermined period of time or timeframe (for example, 200 milliseconds) or if the current sensing system 150 detects a high current on the primary or external side, the power control system will turn off power transmission. The power control system will then attempt to recover control by periodically causing bursting of power via external coil 130 for a defined length of time (for example, for 50 milliseconds once every second). If the power burst is successful and secondary or internal system 200 powers on, primary or external system 100 will receive a communication signal (for example, either high voltage, low voltage, or watchdog/supervisory as describe above). If the power burst is unsuccessful, external system 100 may, for example, wait for a period of time (for example, one second) and burst power again via external coil 130.

In the case that external system 100/external coil 130 has been purposely removed, several mechanisms or methodologies may be used. For example, external battery pack 120 may be removed, which will remove power from external system 100. Removing power from external system 100 means that it will no longer attempt the burst mode recovery of power control for secondary system 200. Furthermore, external system 100 may include an on/off switch or controller. If the user/wearer turns external system 100 off or places it in an off state, external system 100 will no longer attempt the burst mode recover of power control for secondary system 200. External system 100 may even power itself off automatically after a period of time (for example, 10-15 minutes) to conserve battery life. In such cases, external system 100 may automatically attempt to reestablish control of secondary system at power-up. In another embodiment, external system 100 may include a timeout, such that if remote control via bursting cannot be reestablished after a period of time (for example, one minute) of attempting to reestablish control, external system 100 may stop attempting and inform the user via some audible, visual, or tactile signal (for example, an LED, a text display, spoken phrases, etc.). External system 100 would inform the user that control could not be reestablished and provide instructions to the user to re-enable the attempt when ready by, for example, pressing a button or taking some other action. Taking the action (for example, pressing the button) would re-enable the burst mode for another length of time (for example, 1 minute) of periodic attempts (for example, every second). This methodology would, for example, cover the case wherein, for example, the wearer removes external system 100 for a five-minute shower without powering external system 100 down or removing battery pack 120 and would prevent unnecessary transmission attempts and drain on battery pack 120 while external system 100 was powered but control of internal system 200 could not be reestablished.

In a number of embodiments of a sequence or methodology during initial powering up of implanted system 200, first external controller 110 may, for example, provide a "burst" of power via external coil 130 and monitor for a response/signal from implanted system 200 (for example, a higher-voltage or charged signal or a "reset supervisory time" signal). If such a signal is received, first external controller can determine that internal system 200 has properly powered on and initialized in response to the power burst from external system 100. If no signal is received, the first external controller may, for example, disable the power (de-energize external coil 130) to avoid a high current situation, wait for a short period time, and then attempt the power burst again. Using this protocol or methodology, first external controller 110 can automatically recover control of internal system 200 if, for example, external coil 130 and internal coil 230 become misaligned for a short period of time and are then realigned. This methodology can assist in reducing the requirement of operator intervention and/or reduce the occurrence of false misalignment signals for short, transient misalignment events.

In a number of embodiments, data transmitted via the power control or feedback system can be transmitted and/or received separately from external coil 130 and/or internal coil 230, for example, using coils separate from external coil 130 and internal coil 230 or using communication systems other than inductive coils. To conserve space, separate coils may, in a number of embodiments, be wound in the same volume as external coil 130 and internal coil 230. FIG. 3B illustrates schematically an external data coil 130a wound within the same volume as external power coil 130 and an internal data coil 230a would within the same volume as internal power coil 230a. In certain embodiments, it may be advantageous to have the internal coil used for both power and communications and have separate coils external for communications and power. Having separate external coils may, for example, simplify the external circuitry or reduce noise caused by the power or communication signal to the other signal, It is desirable for the size, power consumption and heat generation of components of implanted system 200 to be minimized. In a number of embodiments, the frequency for transmission of the lower voltage signal, the higher-voltage signal and the reset-supervisory-timer or supervisory signal was chosen to be approximately 13.56 MHz. Other frequencies can be used, however. A frequency of 13.56 MHz is not often used in a medical or hospital settings, reducing the likelihood of interference. Further, a frequency of 13.56 MHz is significantly different from the frequency range used for power transfer between external coil 130 and internal coil 230, simplifying any required filtering or separation. Additionally, 13.56 MHz does not substantially radiate from the primary coil 130 or the secondary coil 230 as a result of the small coil size compared to the wavelength, meaning that the primary coil 130 or the secondary coil 230 do not create a source of interference. Therefore, by reciprocity, the 13.56 Mhz system is not significantly affected by sources of interference in the same frequency band. Although there are numerous discrete and integrated circuit approaches for designing 13.56 MHz generators and receivers, many such circuits are relatively large, consume significant power and/or generate significant heat.

In a number of embodiments, each of first external communication system 170 and first internal communication system 270 of system 10 included a radio frequency receiver 172 including a commercially available radio frequency identification or RFID reader chip and/or a radio frequency generator or transmitter 170 including a commercially available RFID reader chip. RFID reader chips are designed to be small and consume low power. However, such RFID reader chips are not designed to be used as pairs in which the RFID reader chips communicate therebetween in transmit-receive communication applications. To the contrary, RFID readers are designed to communicate with RFID tags, which are designed or programmed to store data on thereon which can be read by the reader when the RIFD tag receives an electromagnetic energy signal from the reader. Using power from an internal battery (in the case of an active or semi-active RFID tag) or power harvested from the reader's electromagnetic field (in the case of a passive RFID tag), the RFID tag sends a radio frequency signal back to the reader. In a number of embodiments hereof, commercially available RFID reader chips 172 and 272 were programmed for a novel transmit-receive, chip-to-chip communication configuration in which internal RFID reader chip 272 was caused by first internal controller 210 to transmit a radio frequency signal via internal coil 230 and external coil 130 to external RFID reader chip 172, which communicated the signal to first external controller 110. In a number of embodiments, a high pass filter or a band-pass filter, a 50 ohm impedance matching network, a 13.56 MHz L-C bypass and a DC block were used in each of first internal communication system 270 and first external communication system 170 to couple the 13.56 MHz signals through internal coil 230 and external coil 130. The 13.56 MHz L-C bypass (not shown) was across the H-Bridge and bridge rectifier to short them at 13.56 MHz so they do not affect communications. In the embodiment described, the secondary or internal side is transmit only and the external or primary side is receive only, but both could be implemented as transceivers for bi-directional communications.

An example of an RFID reader chip suitable to be adapted for use in first internal communication system 270 and in first external communication system 170 is the TRF7960 RFID reader, available from Texas Instruments of Dallas, Tex. The TRF7960 RFID readers can be used as general-purpose 13.56 MHz analog transceiver front ends by enabling a direct mode feature of the chip. The direct mode feature of the TRF7960 bypasses the ISO RFID protocol encoders and decoders thereof so that a connected microcontroller can transmit and receive data directly using the chip's on-board RF modulator. Transmitter chip or RF generator 272 can, for example, be configured such that it generates the 13.56 MHz RF envelope at full power by sending the appropriate configuration commands to transmitting RFID reader chip 272 via its serial peripheral interface (SPI) bus. Transmitting RFID reader chip 272 is configured to use an on-off keying scheme when modulating the RF envelope, and it is configured into direct mode. Receiving RFID reader chip 172 is configured to expect an on-off keying scheme, and it is configured into direct mode, but it is not configured to generate a 13.56 MHz RF envelope, as this would conflict with the envelope generated by transmitting RFID reader chip 272. Instead, receiving RFID reader chip 172 is configured such that its receive circuitry is enabled. This mode is typically intended to allow a reader to measure an external RF field to determine if another reader is transmitting so that anticollision measures may be taken. In the present case, however, the measurement mode allows receiving RFID reader chip 172 to sense the 13.56 MHz envelope generated by transmitting RFID reader chip 272 and to receive data as transmitting RFID reader chip 272 modulates that envelope. In a number of embodiments, the signal from the transmitting and/or receiving RFID reader chip 272 is amplified.

First internal controller 210 (the transmitting microcontroller) can, for example, send data by toggling the MOD pin presented by transmitting RFID reader chip 272. When the MOD pin is toggled, the RF envelope is modulated to produce bits (ones and zeroes) using the on-off keying scheme. To simplify the transmission of data from first internal controller 210, the MOD pin can, for example, be wired to the transmit pin of a standard universal asynchronous receiver/transmitter (UART) of first internal controller 210. This conformation allows the software executing on first external controller 210 to use the UART hardware to manage the complex and critical timing required for binary data transmission.

First external controller 110 (the receiving microcontroller) can, for example, receive data via an input/output or IO pin presented by receiving RFID reader chip 172 (for example, the IO_6 pin of the TRF7960 chip). The IO pin represents the demodulated bit value described by the RF envelope and is configured to expect an on-off keying scheme. To simplify the reception of data by first external controller 110, the IO pin can be wired to the receive pin of an UART of first external controller 110. This conformation allows the software executing on the first external controller 110 to use the UART hardware to manage the complex and critical timing required for binary data reception. Use of the UART eliminates the need for software coding and transmission control.

Electromagnetic inductive power transmission of the type described herein can generate significant electromagnetic interference, resulting, for example, in failure to meet regulatory requirements. In a number of embodiments, system 10 and other systems hereof mitigate problems associated with electromagnetic interference by utilizing spread spectrum frequency modulation for power transmission. The spread spectrum modulation may be, but is not limited to, frequency hopping spread spectrum (FHSS) or direct sequence spread spectrum (DSSS). In that regard, power is transmitted by external system 100 via external (primary) coil 130 at frequencies varying or spread within a range of frequencies under control of a spread spectrum algorithm. In a number of embodiments, the frequency may, for example, be varied or spread between approximately 120 kHz and approximately 130 kHz or between approximately 120 kHz and approximately 126 kHz. In several such embodiments, the power transmission is, for example, cycled from approximately 120 KHz to approximately 126 KHz at 1 millisecond (or ms) intervals to achieve a nominal 123 KHz transmission frequency. In a number of embodiments, the nominal power transmission frequency is between 50 and 500 kHz. Use of frequency spread spectrum hopping modulation "spreads" the fundamental and harmonic energy across a number of frequency band channels on a wider electromagnetic spectrum, resulting in, for example, decreased narrowband interference and lower average power per channel. In a number of embodiments, the average RF emissions generated are less than 25 μV/m at 300 m. The decreased narrowband interference enables system 10 to transmit relatively large amounts of power (for example, greater than 20 watts, greater than 30 watts, or often between approximately 30 to 60 watts) as required by implanted device 300 while meeting regulatory requirements for generated electromagnetic noise and interference. Although spread spectrum technology is known, the high Q or quality factor associated with transcutaneous energy transmission via primary and secondary coils has previously prevented its use in transcutaneous energy systems. In other words, it was previously believed that broadband power transmission was not feasible for transcutaneous energy transmission.

The system described herein was designed to have a low Q through selection of the coil inductance to facilitate the use of spread spectrum frequencies. A simple series RLC circuit has a Q of $$Q = 1/R\sqrt{\frac{L}{C}} \cong \frac{f_0}{BW_{3dB}} \quad (1)$$

and a resonant frequency of $$f_0 = \frac{1}{2\pi\sqrt{LC}} \quad (2)$$

Combining (1) and (2) yields $$BW_{3dB} = \frac{R}{2\pi L} \quad (3)$$

In the above equations, Q is the quality factor, $BW_{3dB}$ is the half power bandwidth, $f_0$ is the resonant frequency, R is the circuit resistance, L is the circuit inductance and C is the circuit capacitance.

As can be seen by these equations, maximizing the resistance and minimizing the inductance produces the greatest bandwidth. However, for an inductively coupled system transferring 10's of watts of power, maximizing the resistance produces unmanageable voltage levels and minimizing the inductance limits the effectiveness of the inductive coupling. As an example, with 30 Watts delivered to the load at 15V nominal, the equivalent resistance seen at the output of the secondary coil is only 7.5 ohms.

Figure 4A:
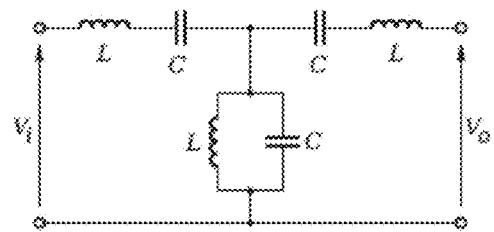
FIG. 4A illustrates an example of a typical band-pass filter used to model the inductive coupling system.
Figure 4B:
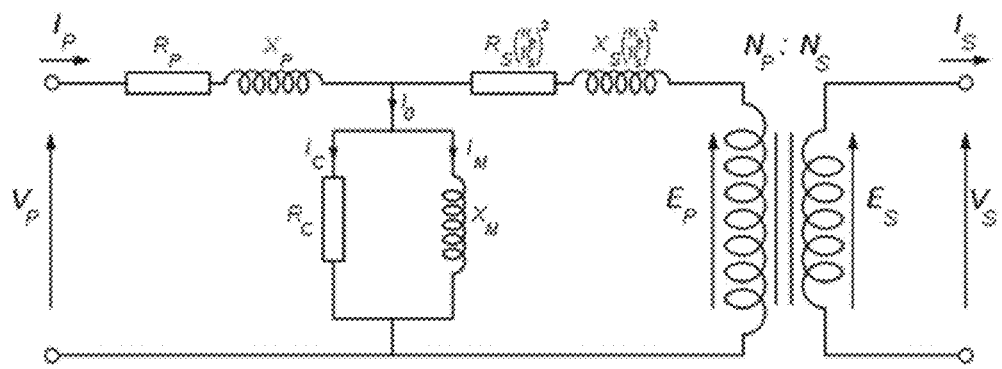
FIG. 4B illustrates an equivalent circuit of a transformer wherein the transformer has the structure of a band-pass filter, and wherein capacitors are added in series with the leakage inductances, $X_P$ and $X_S$.

For this reason, the inductive coupling system was not simply designed to resonate each side of the coupling transformer as done in previous systems. Rather, the inductive coupling system was modeled and designed as a band-pass filter. An example of a typical band-pass filter is illustrated in FIG. 4A. Examining the equivalent circuit of a transformer (see FIG. 4B) shows that the transformer has the structure of a band-pass filter when capacitors or tuning capacitors are added in series with the leakage inductances, $X_P$ and $X_S$. In general, the tuning capacitors and the leakage inductances form series elements of the band-pass filter and the magnetizing inductance forms a shunt element. By selection of the inductance of the transformer, the leakage inductance and additional capacitors can be used to create a bandwidth wide enough to support a spread spectrum signal. Also, for an air core transformer, which is used in several embodiments of the systems hereof, the core losses are zero, meaning $R_C$ can be removed from the model leaving only the magnetizing inductance $X_M$. In a number of embodiments, external or primary system 100 and internal or secondary system 200 are adapted such that a change of frequency of energy is transmitted from external coil 130 to internal coil 230 of +/−10% results in a change in transfer efficiency of no greater than or less than 10%.

Because the systems hereof include a primary and secondary designed to have a low Q (defined in Equation 1 above as $f_0/BW_{3dB}$), spread spectrum signals can be used without the need to adjust the resonant frequency or the center frequency of the system. In other words, the system does not require retuning to use frequency hopping signals. As a result, in a number of embodiments, the system may include set or fixed tuning capacitors rather than a cumbersome and power-consuming reconfigurable tuning network. Moreover, because the system may have a set of fixed resonance, the primary driver can adjust the frequency (frequency hop) of the power transmission signal without informing the secondary of the frequency change.

Additionally, because the system has a low Q (broad bandwidth), sophisticated spread spectrum signals can be used that have more than one frequency component at a given time such as direct sequence spread spectrum. In a number of embodiments hereof, the Q of the system is less than 100, less than 50, less than 10, or even less than 5. In a number of such embodiments, the Q of the system is less than 10 or less than 5.

In a number of embodiments hereof, the resonant frequency of the primary coil and/or the secondary coil (and, thus, the center frequency of the spread spectrum power transmission signal) may be adjusted in response to, for example, misalignment of the primary coil and the secondary coil, in response to changes in component values which may drift with time, or in response to the temperature of the external system. Tuned capacitors may, for example, drift in value over their lifetime as a result of factors such as moisture absorption. The tuning of the primary coil and/or the secondary coil may be adjusted in response to, for example, misalignment of primary coil and secondary coil, in response to changes in component values which may drift with time, or in response to the temperature of the external system. In such embodiments, a reconfigurable tuning network may, for example, be used. After any such adjustment in resonant or center frequency, the spread spectrum algorithm may be centered around the new resonant frequency. As frequency changes during spread spectrum algorithms hereof, however, there is no need to tune either the primary coil or the secondary coil to the various frequencies used in the spread spectrum algorithm.

Figure 4C:
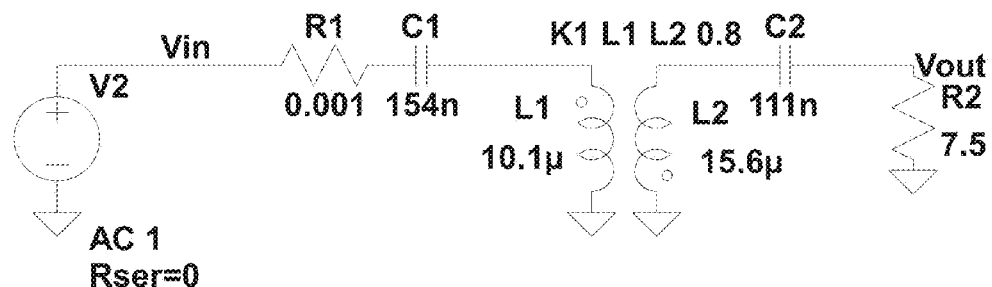
FIG. 4C illustrates a simulation schematic for the inductive coupling system.
Figure 4D:
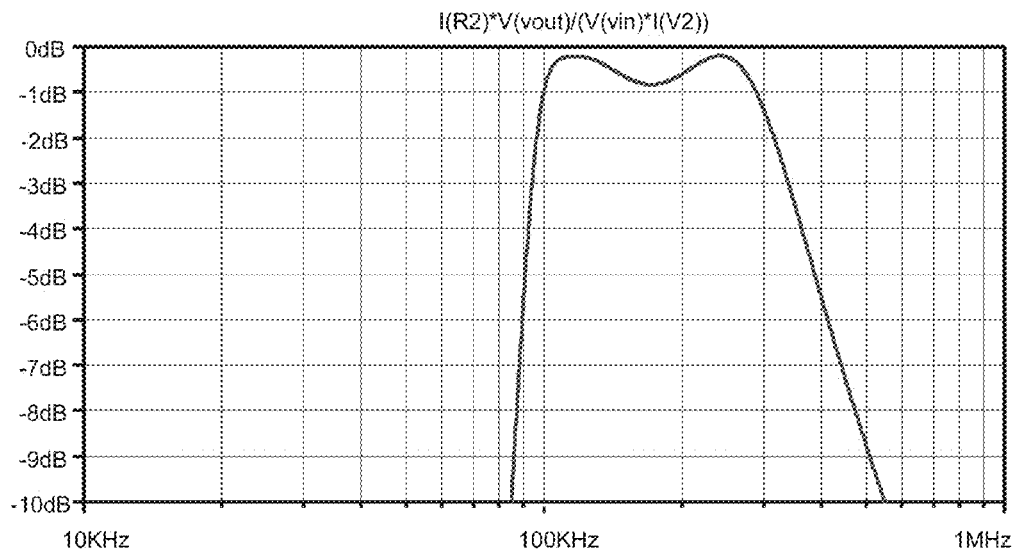
FIG. 4D illustrates a graph of simulation results demonstrating that the transfer efficiency from Vin to Vout is good from 100 kHz to almost 300 kHz.
Figure 4E:
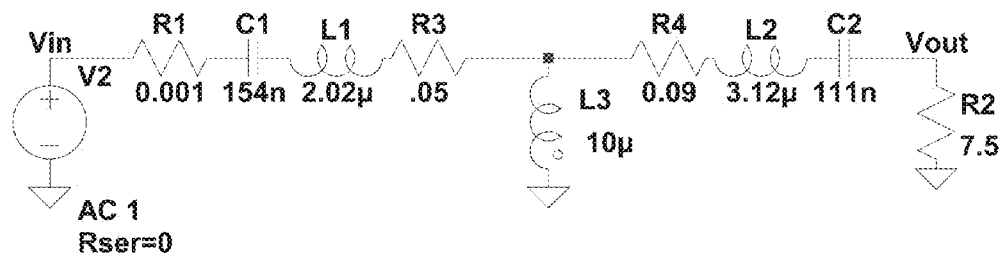
FIG. 4E illustrates a simulated band-pass model of the inductive coupling system.
Figure 4F:
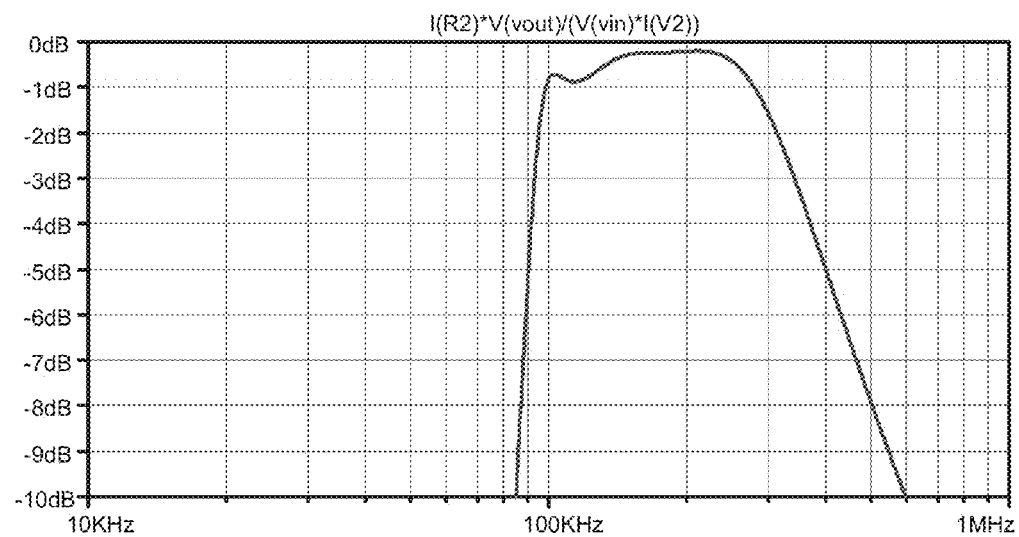
FIG. 4F illustrates a graph showing agreement between the band-pass model results and the transformer simulation results.

A simulation schematic for the inductive coupling system designed is shown in FIG. 4C. For simulation purposes, the coupling coefficient was assumed to be 0.8 to model the leakage inductances, and the load was 7.5 ohms (30 Watts at 15V). The equivalent series resistance (ESR) of each coil was included in the transformer model. The results can be seen in FIG. 4D, which shows that the transfer efficiency from Vin to Vout is very good from 100 kHz to almost 300 kHz. A simulated band-pass model of the inductive coupling system can be seen in FIG. 4E, where the leakage inductances have been assumed to be 20% of the coil inductances and the magnetizing inductance as 10 uH. As can be seen in FIG. 4F, the band-pass model results show very good agreement with the transformer simulation.

Figure 4G:
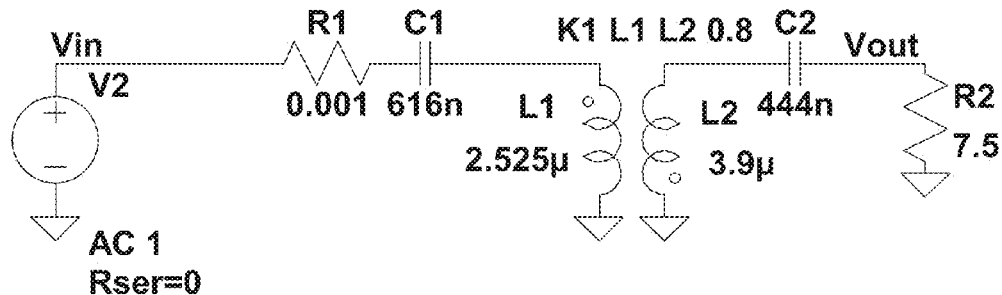
FIG. 4G illustrates another schematic model wherein, to ensure resonance at 125 kHz, the capacitors were increased by a factor of four to keep the same resonant frequency as FIG. 4C.
Figure 4H:
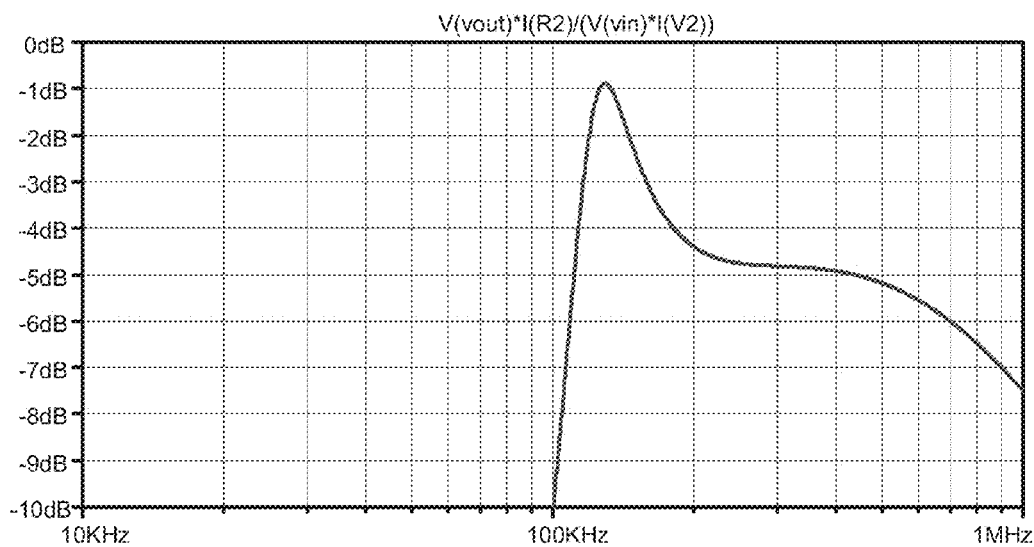
FIG. 4H illustrates a graph of simulation results showing a resonance at 125 kHz, but wherein the bandwidth is comparatively narrow.

To demonstrate the importance of designing the inductive system using a band-pass filter model, the system in FIG. 4C was modified by scaling the transformer inductances down by a factor of four. Equation 3 would suggest, although the system is not a simple RLC, that reducing the inductance should increase the bandwidth. To ensure resonance at 125 kHz, the capacitors were increased by a factor of four to keep the same resonant frequency as FIG. 4C as calculated using Equation 2. The schematic can be seen in FIG. 4G. The results shown in FIG. 4H show a resonance at 125 kHz as predicted by Equation 2 but the bandwidth is comparatively very narrow. This analysis demonstrates that the inductive coupling system is beneficially designed to resonate and be constructed as a band-pass filter to have sufficient bandwidth to support a spread spectrum signal.

Figure 5A:
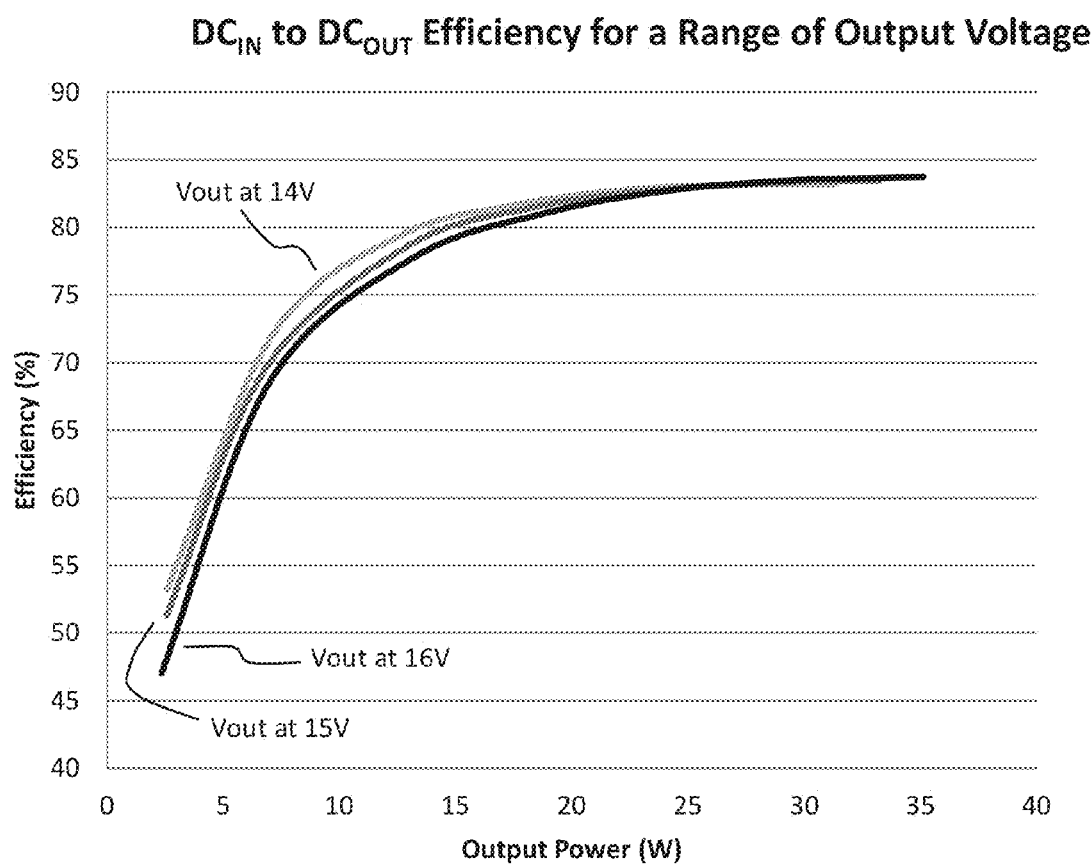
FIG. 5A illustrates a graph of efficiency as a function of output power for a range of output voltages.

FIG. 5A shows that the maximum conversion efficiency is achieved by maintaining the output power at 30+ Watts (maximum load). However, when lower power is required at the load, reducing the output power by changing the primary drive voltage reduces the conversion efficiency. Therefore, it is more efficient to enable the power transfer at a power level of 30+ Watts and then disable the transmission for a given period of time. In a number of embodiments, the transfer efficiency of the system (where transfer efficiency is defined as $P_{OUT-DC}/P_{IN-DC}*100$) is greater than 75%, greater than 80% or greater than 85%. During the disabled time, a capacitance on the secondary (internal) side of the inductive transfer can provide power to the load (implanted device). When additional power is required, the primary (external) side can be enabled to recharge capacitor system 250. In general for power levels around 30 Watts, any capacitance designed into the secondary or internal system with reasonable physical size for the load (implanted device 300) will be insufficient to operate the load for any appreciable time period. Therefore, the primary will frequently be enabled or energized and disabled to provide power to the secondary. For example, in a number of embodiments the internal secondary system may function for only less than one second before requiring capacitor system 250 to be recharged by the primary. As described above, system 10 is designed to hold the voltage on capacitor system 250 within a voltage window having a lower and upper threshold. The system efficiency is designed so the transfer efficiency is not affected by the exact voltage level seen on capacitor system 250. This can be seen on the graph of FIG. 5A by examining the conversion efficiency at 30+ Watts for 14, 15, and 16 volts.

FIG. 5B illustrates changes in the power requirements of the load (implanted device 300), the external/primary output voltage and the voltage of the internal/secondary capacitor system 250 over a period of time for several embodiments hereof. As illustrated, the power requirement of the implanted device 300 is initially approximately 100%. Power is transferred via primary or external coil 130 via bursting or on/off cycling of external coil 130 (done, for example, by On-Off keying or On-Off modulating the power transmission frequency, or enabling-disabling the primary driver or H-bridge driver) at a predetermined power or voltage amplitude (or amplitude range) sufficiently high to provide a predetermined efficiency (for example, at least 75% or at least 80%). In general, it is desirable to maximize efficiency. After a period of time, the power requirement of implanted device 300 decreases to 50% in FIG. 5B. As illustrated in FIG. 5B, the amplitude and frequency of the voltage output of external coil 130 is maintained at the predetermined amplitude (or amplitude range), but the duration of the power bursts decreases as compared to the case of a 100% power requirement. After a period of time, the power requirement of implanted device 300 further decreases to 10% in FIG. 5B. Once again, the amplitude and frequency of the voltage output of external coil 130 is maintained at the predetermined amplitude (or amplitude range), but the duration of the power bursts decreases as compared to the case of a 50% power requirement. Upon the power requirement of implanted device 300 increasing from 10% to 100% in FIG. 5B, the amplitude and frequency of the voltage output of external coil 130 is maintained at the predetermined amplitude (or amplitude range), but the duration of the power bursts increases. Preferably, the duration of the power bursts is at least several cycles at the center frequency of the spread spectrum signal. As described above, capacitor system 250 operates in a manner similar to a filter capacitor to filter the rectified spread spectrum signal and to filtering the frequent bursts of energy to provide a DC voltage in a predetermined range of voltages to implanted device 300. The amplitude of the power or voltage output of the external system 100/external coil 130 can, for example, be maintained within 20% of full power, within 10% of full power or at full power when external coil 130 is energized.

Figure 5C:
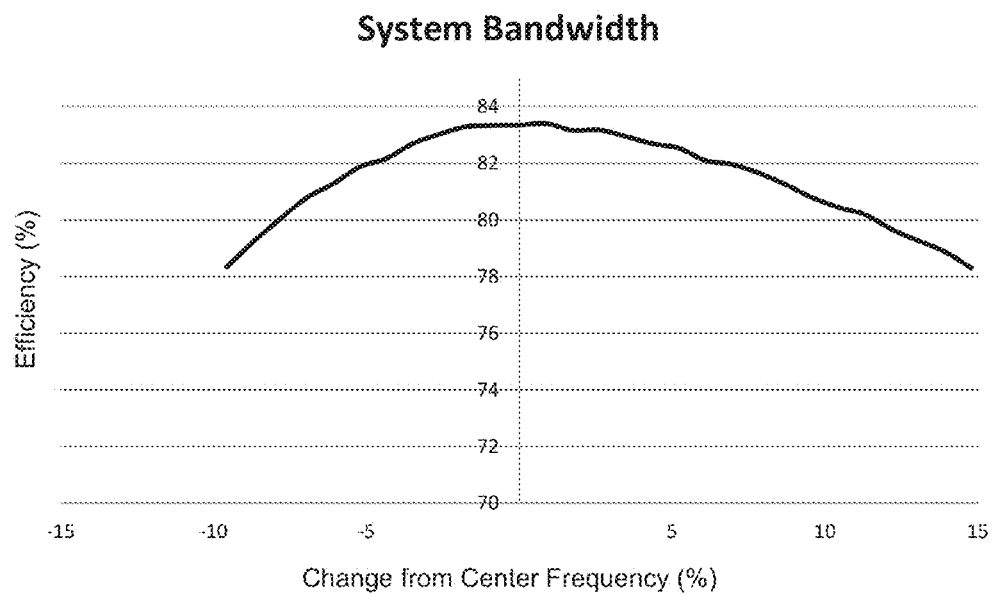
FIG. 5C illustrates a graph of efficiency as a function of the change from center frequency.

As described above, system 10 is designed to transfer power using spread spectrum signals. FIG. 5C shows that the bandwidth of system 10 has been designed to have a low enough Q to enable spread spectrum transfer. As can be seen, a ±10% change in the frequency compared to the center frequency reduces the transfer efficiency by only approximately three to five percentage points which is less than 10%.

Figure 5D:
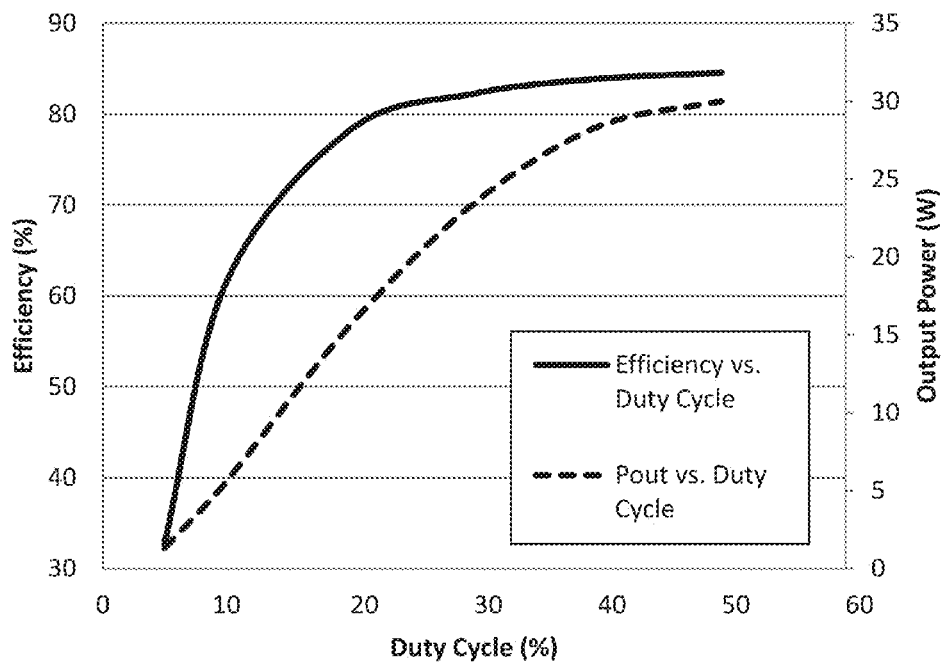
FIG. 5D illustrates efficiency as a function of duty cycle and output power as a function of duty cycle.

Previous solutions have varied the duty cycle of the H-bridge fundamental drive frequency to adjust the output power. As can be seen from FIG. 5D, reducing the duty cycle reduces the amount of power delivered to the load, but it also reduces the transfer efficiency of the system which is undesirable because it generates unwanted heat (loss) and reduces the run-time of the primary side battery pack.

Figure 6:
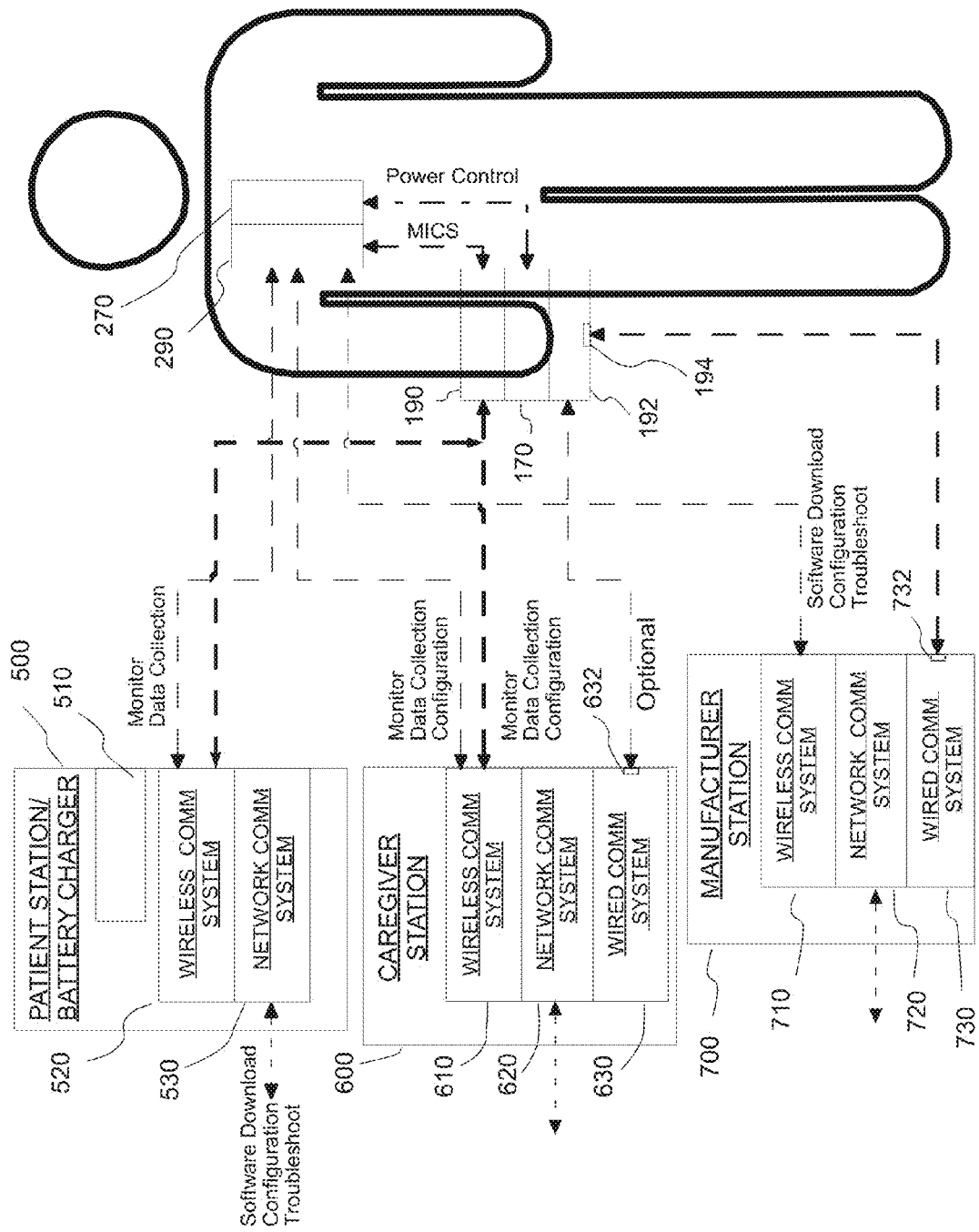
FIG. 6 illustrates a schematic representation of the system of FIG. 1A or 1B as part of an overall patient care system.

As described above, the internal control system of internal system 200 can, for example, include second internal controller 220 (including, for example, a microcontroller or microprocessor) to monitor and control implanted device 300. Either first internal controller 210 or second internal controller 220 can also, for example, monitor one or more sensors, sensor systems or sensor arrays 280 and/or 280' that can include one or more sensor (for example, pressure sensors, flow sensors, force sensors, temperature sensors, pH sensors etc.). To enable external monitoring and/or control of implanted device 300, sensor system 280 and/or other internal or implanted components, internal system 200 can, for example, include a second internal communication system 290. External monitoring and/or control of various internal system components can, for example, be accomplished using wireless (for, example, radio frequency) communication between second internal communication system 290 of internal system 200 and one or more external communication systems/external controllers, including, for example, second external communication system 190 and first external controller 110 of external system 100. The frequency used for communication between second internal communication system 290 of internal system 200 and one or more external communication systems/external controllers can be different from the frequency range of power transmission and different from the frequency range of communication between first internal communication system 270 and first external communication system 170. A frequency range of 402 MHz-405 MHz has, for example, been recommended for medical implant communication systems (MICS) and has been implemented in the United States under the Federal Communications Commission (FCC) rules 47 CFR 95.601-673, and in Europe under the European Telecommunications Standards Institute (ETSI) Standard EN 301 839-1. Remote communications with second internal communication system 290 can, for example, follow the MICS guidelines to transfer digital data bi-directionally between internal system 20, including the internal controller(s) thereof and implanted device 300, and one or more external communication systems/external controllers. Such external communication systems and/or external controllers can, for example, be components of external control system 100, a patient station 500 (which can, for example, include a charger 510 for rechargeable battery 120), a caregiver station 600 (for use, for example, by a physician and/or other caregiver) and a manufacturer station 700 (see FIG. 6). To minimize power consumption, the digital transmission link can be turned off when not in use. A low power wake-up signal (for example, a 2.4 GHz wake-up signal) can, for example, be used to turn on the transmission link. MICS-based internal or implantable communication units and external communication units or base stations suitable for use herein are for example, available from Zarlink Semiconductor Inc. of Ottawa, Canada.

Using, for example, MICS, second internal communication system 290 and/or second external communication system 190 can establish a relatively high-speed, longer-range (up to, for example, approximately 2 meters) wireless link between internal system 200 and patient station 500, caregiver station 600 or manufacturer station 700. The wireless communication link can, for example, be used to send patient health and device operating data to bedside patient station 500 via a radio frequency, wireless communication system 520 of patient station 500. Data can, for example, be transmitted or forwarded from patient station 500 via a network communication system 530 (using, for example, landline telephone service, wireless telephone service, the Internet etc.) to, for example, caregiver station 600 via a network communication system 620 of caregiver station 600. When the patient is in the caregiver's office or otherwise in the vicinity of caregiver station 600 (which, can for example, include a specific or general purpose computer), the wireless, digital communication protocol (via communication between a wireless communication system 610 of caregiver station 600 and second internal communication system 290 or second external communication system 190) can be used by the caregiver to, for example, download operating parameters to second internal controller 220 for implanted device 300, to, for example, configure operation of implanted device 300 for patient-specific operation. Alternatively, a wired connection (using, for example, a universal serial bus (USB) connection) can be formed between a port 632 of a wired communication system of caregiver station 600 and a port 194 of a wired communication system 192 of external system 100.

Using manufacturer station 700 (which, can for example, include a specific or general purpose computer), a manufacturer can, for example, use a communication link (via a wireless communication system 710 or a via a communication port of a wired communication system 630) to download operating firmware to second internal controller 220 for implanted device 300 from manufacturer station 700. Manufacturer station 700 can serve as a service and diagnostic station. Manufacturer station 700 can be used to monitor device operational information and to upload device operational "configuration" parameters. Manufacturer station 700 can also include a network communication link 720 to, for example, communicate with external system 100, patient station 500 or caregiver station 600. Manufacturer station 700 can also include a wired connection system 730 (for example, a USB connection) including a communication port 732 to form a wired communicative connection with port 194 of wired communication system 192.

Second internal controller 220 can, for example, monitor and record various parameters of the operation of implanted device 300 over time (similar to a "flight controller") to provide such information to a caregiver and/or a manufacturer (for example, operating voltages, currents etc.). Caregiver station 600 can, for example, be used to program operation of implanted device 300 on a per patient basis. In a number of embodiments, caregiver station 600 can periodically communicate with patient station 500 (for example, nightly) via, for example, the internet to enable a physician or other caregiver to monitor patient and device status over extended periods of time.

Figure 7:
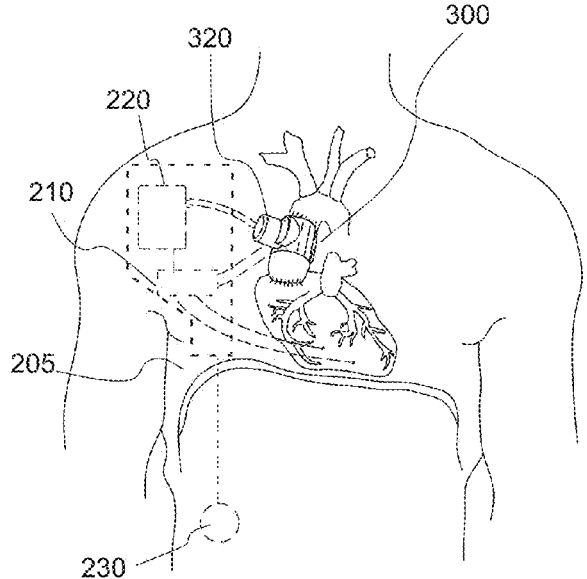
FIG. 7 illustrates use of the system such as the systems of FIG. 1A or 1B in connection with an implanted blood flow assist system placed in line with the ascending aorta of a patient, wherein the system is illustrated schematically.

As discussed above, in a number of embodiments, implanted device 300 is a blood flow assist device as, for example, described in U.S. patent application Ser. Nos. 3/370,113, 13/370,137 and 13/370,155 and PCT International Patent Application No. PCT/US2012/024572. Such assist devices are moving valve heart assist pumping systems 300 which may, for example, be placed in line with a blood vessel such as the ascending aorta as illustrated in FIG. 7. In pump system 300, motor 320 imparts reciprocal motion to a valve assembly 330 including closure members 332 which close upon forward motion of valve assembly 300 (relative to blood flow from the heart through pump system 300) and open upon rearward movement of valve assembly 330 (see FIG. 8). Valve assembly 300 can, for example, be connected in the vicinity of the perimeter thereof to a flexible conduit 304 through which blood flows.

Figure 9:
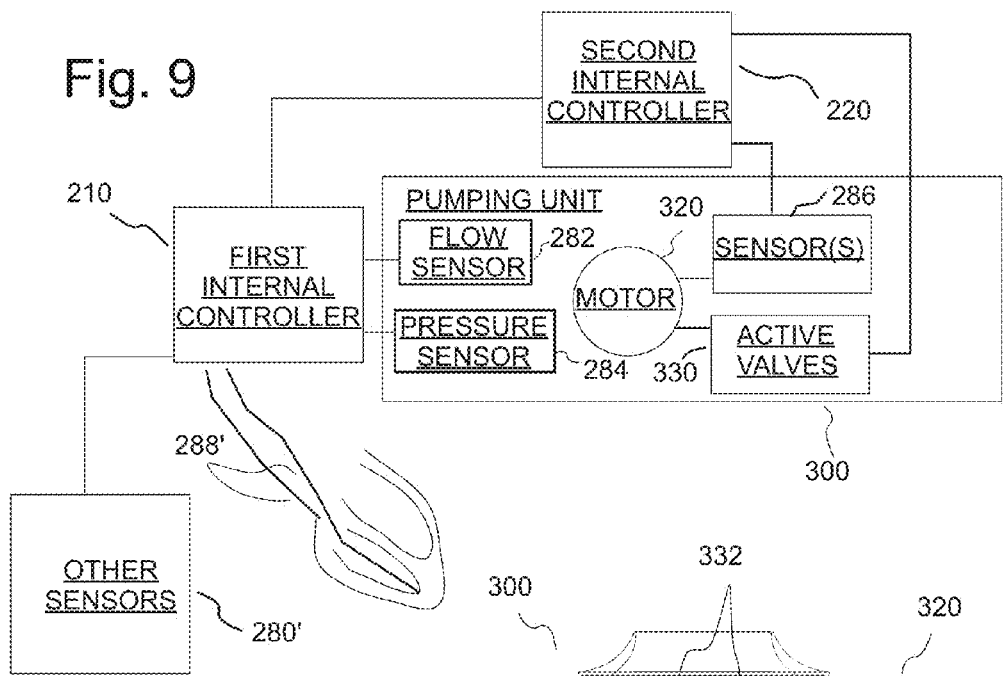
FIG. 9 illustrates schematically a portion of the system such as the systems of FIG. 1A or 1B including a moving valve pump system.

Control parameters of pump system 300 that can, for example, be adjusted by a caregiver via caregiver station 500 include, but are not limited to, timing and/or frequency of the movement of valve assembly 330. In the case that a pacemaker functionality is included (for example, as a components of second internal controller 220), pacing of the heart can also be adjusted by a caregiver. Various sensors can be used in connection with pump system 300 such as a flow sensor 282 (for example, a thermistor) and a pressure sensor 284, each of which can be placed in fluid connection with the flow path of blood through pump system 300 (see FIGS. 8 and 9). Various other sensors 286 can, for example, be placed in operative connection with pump system 300 (for example, a current sensor in operative connection with motor 320, a force sensor in operative connection with valve assembly 300, etc.) to measure various operational parameters of pump system 300. Leads 288' can be placed in operative connection with the heart of the patient can be used to sense the electrical activity and rate of the heart for use in timing of the movement of valve assembly 330. For example, the P wave of the heart electrocardiogram or a portion of the QRS complex can be used to time valve movement. Leads 288' can also be used in pacing the heart. Other sensors 280' can, for example, measure various patient physiological sensor (for example, atrial pressure, left ventricle pressure, temperature, respiration variables etc.). As illustrated in FIG. 9, sensors as described above can be placed in communicative connection with first internal controller 210.

In a number of embodiments as described above, various sensor leads were connected to first internal controller 210 and not to second internal controller 220, which controls pump system 300. This division can, for example, be effected to allow second internal controller 220 to focus its activity upon implanted device/pump system control. As described above, pump system (and/or other implanted device) control, sensor monitoring, communication control etc., can be accomplished via a single controller or such tasks can be distributed over two or more controllers. Moreover, various signals can be redundantly routed or split between two or more microcontrollers.

A caregiver can, for example, observe measures of flow and pressure (and/or other measured properties of blood or parameters of pump system 300), either during blood flow assist or absent blood flow assist. With the valve assembly 330 of pump system 300 set in the "off" mode, the valve assembly is stationary and in an open state, the caregiver can observe the patient's unassisted blood flow profile and caregiver station 500 can, for example, integrate the flow signal to calculate heart stroke volumes as well as cardiac output expressed in liters per minute or LPM terms. The caregiver can then add moving valve assist by activating valve assembly 330 using, for example, test modes and timing adjustments to determine which moving valve operating mode is best for the patient (for example, to provide a determined or desired assisted cardiac output). Either or both of first external controller 110 or second internal controller 220 can then be programmed for automatic moving valve operation as the patient leaves the caregiver's/physician's environment.

Output from sensors which provide a measurement of one or more parameters of the blood (including, for example, parameters of blood flow) such as sensors 282 and 284 and/or other sensors can be used in setting parameters for pump system 300 as well as for providing closed-loop control of pump system 300. As known in the computer arts, control algorithms, which can include artificial intelligence routines, can be programmed into the processors (for example, microprocessors) of system controllers, including, for example, if-then statements, as well as other types of automatic logical control.

In addition to physiologic output signals such as flow and pressure, motor performance parameters or signals can also be sensed and periodically recorded. These signals can, for example, include or be related to motor current, motor commutation, timing events, as well as motor speed and its derivatives of valve speed, valve position and valve acceleration. These signals can, for example, be transmitted to second internal controller 220 via implanted leads connecting second internal controller 220 to pump system 300 and to the patient's heart. Using the known relationship of motor current to motor torque, the system will be capable of determining the force being supplied to the moving valve. By additionally determining/measuring the pressure behind the valve, the system will be capable of, for example, calculating the pressure difference across valve assembly 330. The pressure difference across valve assembly 330 can also be measured more directly using an appropriate sensor or sensors. This pressure difference when multiplied by valve assembly velocity and integrated during the forward stroke of valve assembly 330 provides valve assembly work and power information. With pump system 300 off, flow and pressure sensing similarly provide unassisted heart work and power performance information. With pump system 300 on, the relative energy contributions of the heart and pump system 300 can be calculated and the operating parameters of pump system 300 can be adjusted to provide the best possible outcomes for the patient as judged by the caregiver.

Figure 11:
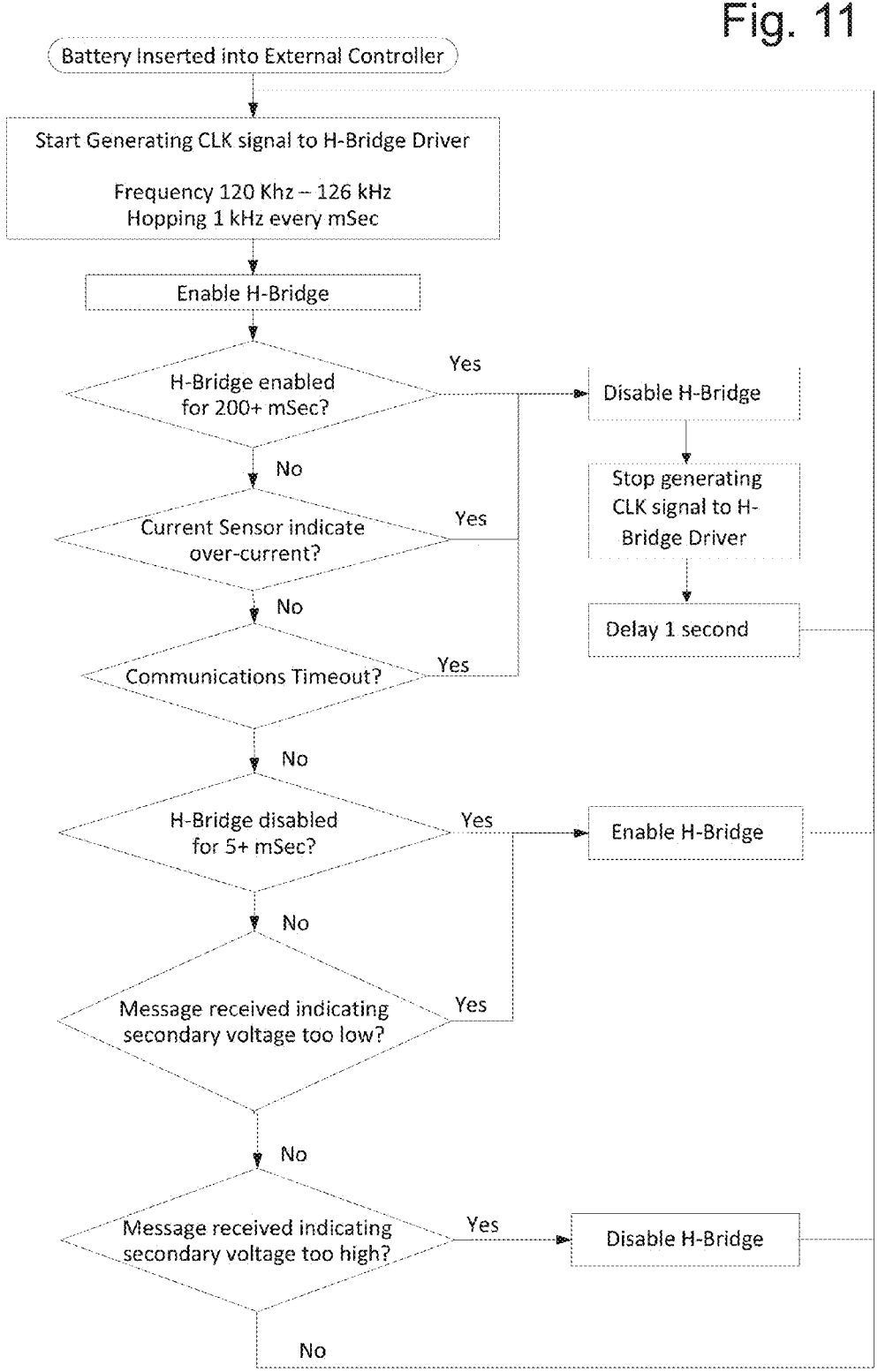
FIG. 11 illustrates a flow chart of an embodiment of a method of operation of the external system of FIG. 1B.
Figure 12:
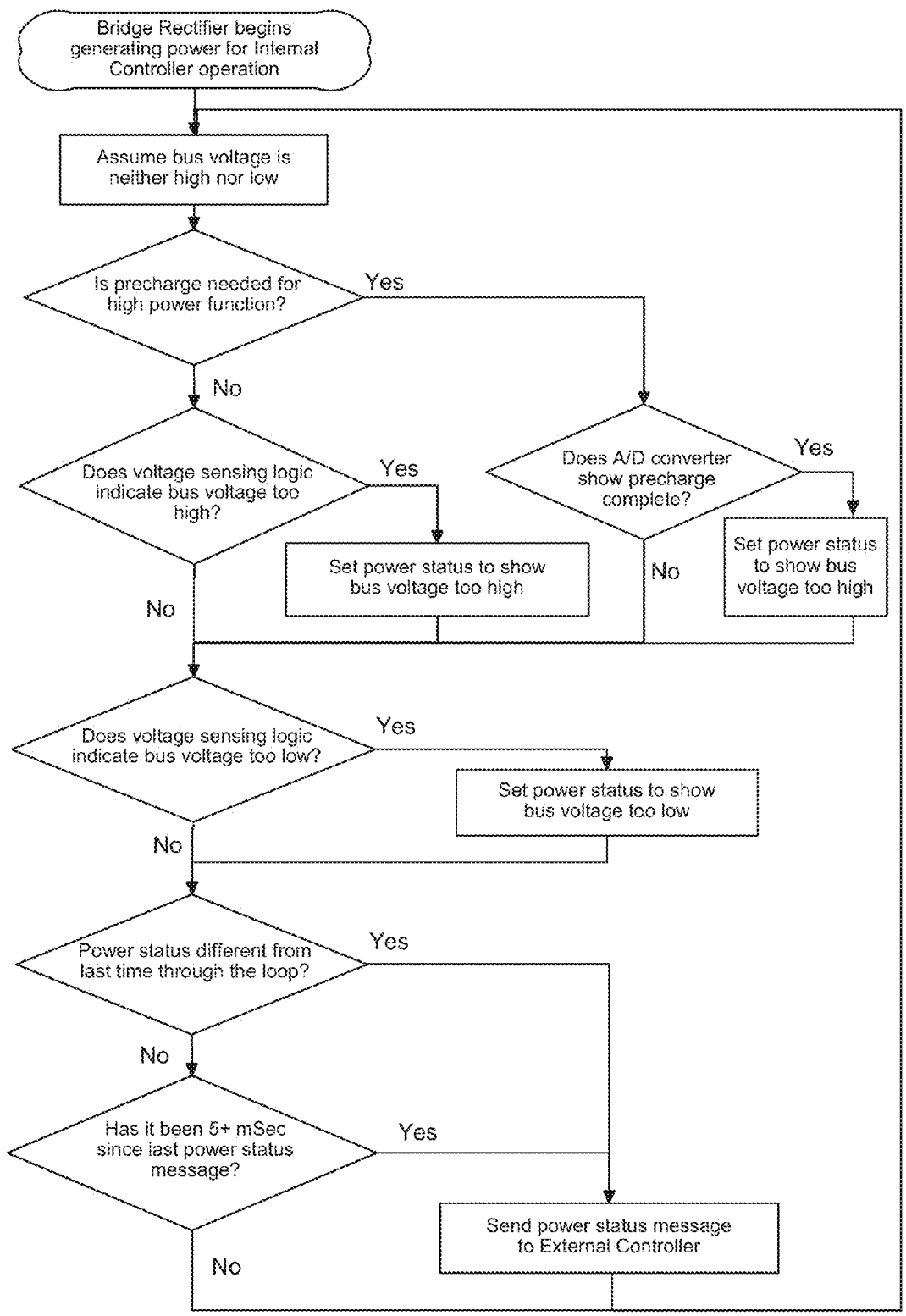
FIG. 12 illustrates a flow chart of an embodiment of a method of operation of the internal system of FIG. 1B.

Referring to, for example, FIGS. 1B, 5E, 11, and 12, in a number of representative embodiments, systems hereof were constructed as shown in FIG. 1B and operated as shown in FIGS. 5E, 11, and 12. In the embodiment of system 10a of FIG. 1B, external system 100a was designed to be powered by, for example, a single battery pack including four series connected rechargeable battery cells, collectively referred to herein as the battery 120, having a fully charged maximum voltage of 16.8V and a fully discharged minimum voltage of 12V. Battery 120a supplied power to three DC/DC converters. More or less than four external battery cells may be arranged in an appropriate series/parallel configuration as known to those skilled in the electrical arts to increase the battery pack operating time between charges and/or operating life without changing the designed operating voltages of the systems hereof. A plurality of redundant external battery packs is not required.

In system 10a, a first DC/DC converter provided 12V to an H-Bridge driver (for example, a model HIP4081A high frequency H-Bridge driver available from Intersil Corporation of Milpitas, Calif. USA). The H-Bridge driver drove NFETS 140a to produce the drive frequency and power supplied to tuned primary coil 130a, which included eight turns of 12 AWG litz wire. Primary coil 130a was designed to resonate with a center frequency of approximately 122.5 kHz with a bandwidth wide enough to cover 120-130 kHz. The resonance was achieved with a single tuning capacitor in series with primary coil 130a. Two tuning capacitors, one on each side of primary coil 130a, may optionally be used to balance the system and to reduce switching noise on primary coil 130a to ensure EMI compliance as, for example, required by the FCC.

A second DC/DC converter provided the power to the H-bridge NFETs 140a that effectively drove primary coil 130a. The 10V output of the second DC/DC passed through a current sensor circuit 150a including, for example, a sense resistor and a current sense amplifier. In a number of embodiments, the current sensor circuit 150a would disable the H-bridge driver if the current exceeded ten amps.

A third DC/DC converter provided the power to an external control system/controller 110a (for example, a microcontroller) and an external communication system 190a (for example, including radio frequency transceiver circuitry) at 3.3V. External controller 110a was used to control the operation of the H-bridge and radio 190a. External controller 110a enabled or disabled the H-bridge driver and supplied the drive frequency to the H-bridge driver. Additionally, the external controller 110a was programmed to frequency hop the drive frequency to the H-bridge driver to, for example, help reduce EMI from primary coil 130a. In a number of embodiments, the frequency hopped from 120 kHz to 126 kHz in 1 kHz steps. The dwell time on each channel was, for example, 1 ms with each channel getting equal active time. At 1 ms, the number of cycles on a channel was equal to 1 ms times the channel frequency. As an example, a 120 kHz drive frequency corresponds to 120 cycles at 120 kHz in 1 ms. Therefore, the output sequence from external controller 110a would be as follows: 120 cycles at 120 kHz, followed by 121 cycles at 121 kHz, followed by 122 cycles at 122 kHz, followed by 123 cycles at 123 kHz, followed by 124 cycles at 124 kHz, followed by 125 cycles at 125 kHz, followed by 126 cycles at 126 kHz, then the sequence is repeated continuously. The resulting average EMI from primary coil 130a was reduced to one seventh of that of a comparable system in which a spread spectrum control algorithm was not used. Additional channels can be added and the bandwidth may be increased. The system may, for example, cover a 10 kHz bandwidth with eleven channels having 1 kHz channel spacing. External controller 110a was also designed to receive commands from external communication system 190a. External communication system 190a was adapted, for example, to receive information/commands from internal system 200a via an internal communication system 290a (for example, including radio frequency transceiver circuitry). In a number of embodiments, the radio frequency communication was in the 915 MHz band and used a robust modulation protocol of direct sequence spread spectrum (DSSS) to help eliminate potential interference from other electronic and wireless devices. Additionally, the DSSS can be frequency hopped to create an extremely robust signal. The 915 MHz DSSS smears the energy in the RF communication signal across a bandwidth greater than 500 kHz. Frequency hopping the DSSS signal moves the center frequency of the smeared signal around in the band. The resulting frequency hopping direct sequence spread spectrum signal becomes very immune to interference. In a number of embodiments of system 10a, communication signals were not transmitted via external coil 130a and internal coil 230a.

Internal system 200a included secondary coil 230a and a series tuning capacitor. The capacitor was used to set the resonant frequency to approximately 122.5 kHz. Two tuning capacitors, one on each side of the secondary coil, may optionally be used to balance the system and to reduce switching noise on the secondary coil to ensure EMI compliance as, for example, required by the FCC. A safety shunt 232a was placed across tuned secondary coil 230a. In a number of embodiments, shunt 232a would activate only in the event of a system failure or error. Shunt 232a, shorts the output of secondary coil 230a to ensure no more energy is provided to internal system 200a which could cause excess heat and potential excess heating of body tissue. Shunt 232a was designed to automatically activate if a 21V over voltage protection circuit 262a was activated for longer than a predetermined period of time. Shunt 232a could also be activated by an on-board temperature sensor.

The output of secondary tuned coil 230a was provided to a full-wave rectifier constructed with low-loss schottky diodes. The output of the rectifier was filtered by a first energy storage system such as a capacitor system 250a including, for example, five 1000 uF 25V electrolytic capacitors. Capacitor system 250a also held a small amount of energy to allow response time for the communication of commands from internal system 200a to external system 100a. The commands were dependent on the voltage on capacitor system 250a. In a number of embodiments, internal system 200a would inform external system 100a when the voltage was above 17V, was below 15V, or when it was between 15V and 17V. The voltage monitoring was done periodically but at a frequency essentially making it continuous monitoring. In several embodiments, the voltage on capacitor system 250 was monitored by two comparators that sent digital signals to internal control system/controller 210a (for example, a microprocessor). Internal controller 210a determined the status and used internal communication system 290a (for example, a 915 MHz DSSS system) to send wireless information/commands to external system 100a (via external communication system 190a). Internal system 200a included a DC/DC converter to transform the 17V signal to 3.3V to run internal controller 210a and radio 290a.

In a number of studies, the efficiency of the power transfer from the 10V DC/DC converter to the output of the rectifier (DC in to DC out) was approximately 90% with 35 W of output power.

Figure 8:
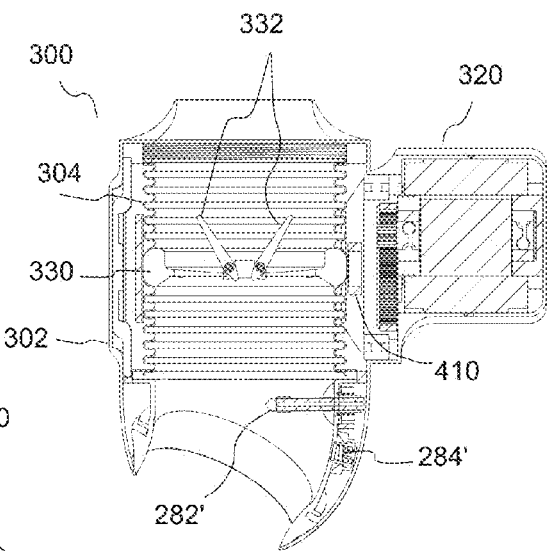
FIG. 8 illustrates an embodiment of an implantable, moving valve pump system for use in connection with a system such as the systems of FIG. 1A or 1B.

The systems hereof are well suited for use in connection with, for example, implantable systems wherein a failsafe mode of operation is provided should an external/primary source of power be removed/deactivated. As described above, in a number of embodiments, internal system 200a includes or is in operative connection with an implanted device such as, for example, moving valve pump system 300. In a number of embodiments, pump system 300 was connected in series with the heart to assist the heart in pumping blood and is designed such that valve assembly(ies) 330 thereof are in a normally open state as described above. In that regard, closure members 332 (which may be biased toward an open state—for example, via springs or other biasing members) close upon forward motion of valve assembly 300 (relative to blood flow from the heart through pump system 300) and open upon rearward movement of valve assembly 330 (see FIG. 8). Valve assembly 300 will open (as a result of biasing and/or the momentum of natural blood flow) if the secondary voltage is lost as a result of, for example, absence or deactivation of the external system 100a. Valve assembly 330 of pump system 300 will open in response to the heart pumping and will not substantially impede blood flow. FIG. 8 illustrates closure members 332 of valve assembly 330 in an open state during, for example, a backstroke of valve assembly 330 or when, for any reason, pump system 300 is not active (for example, because of power loss or failure of one or more components of pump system 300).

The normally open state of valve assembly 330 of pump system 300 reduces or eliminates the need for an internal energy storage unit that could operate pump system 300 without the operating presence of external system 100a. Internal energy storage (via, for example, in internal/implanted rechargeable battery) reduces the lifetime of an internal/implanted device. In that regard, internal energy storage systems require periodic service by surgery. The systems hereof do not suffer from that limitation. The operational power for internal system 200a is continuously supplied in real-time by external system 100a for extended periods of time (for example, for the charge life of battery 120a); and pump system 300, as described above, is designed to not substantially impede the flow of blood therethrough when external system 300 is removed.

In a number of embodiments, closure members of valve assemblies of pump systems hereof are opened and/or closed in an active manner as described in U.S. patent application Ser. No. 13/370,155 and PCT International Patent Application No. PCT/US2012/024572. In that regard, testing demonstrated that actively moving the closure members of a valve assembly toward a closed position to close the valve opening at the beginning of the forward stroke can increase pumping efficiency by approximately 50 percent. Actively moving closure members of a moving valve pump system toward a closed state is thus desirable for the purpose of increasing pump efficiency. As used herein, the terms such as "active" or "actively" refer to control using one or more devices, mechanisms, systems and/or methods for moving closure members toward an open or closed position or state independent of the force asserted upon the closure members by blood flow. Actively moving the closure members of a valve assembly in a moving valve pump system may, for example, be effected using a mechanism or system that activates closure member movement based on the position of the valve assembly.

In a number of embodiments, closure members similar to closure members 332 are used in pump systems hereof wherein the axles, shafts or rods fixed to the closure members are extended to pass through at least a portion of the valve support structure of the valve assembly and to extend outside of the flow conduit of the pump system. FIGS. 10A through 10D illustrate an embodiment of a valve assembly 1300a including a valve support structure 1310a (see FIG. 8A), closure members 1332a and shafts 1332a. Shafts 1332a extend through at least a portion of support structure 1310a so that a portion of shaft 1332a is outside of and/or sealed from the blood flow path through flow conduit 304 of pump system 300 (or another moving valve pump system hereof). A flexible seal 1340a, which can be positioned within a seating formed in support structure 1310a, is fixed to shaft 1332a, which passes through an opening or passage 1342a of seal 1340a.

To assist in providing proper alignment and relatively free movement thereof, each shaft 332a can cooperate with (for example, pass through) one or more bearings. In the embodiment of FIGS. 10A through 10D, each shaft 1332a is mounted within, for example, two rolling element bearings 1350a to properly align each shaft 1332a and minimize torque required to rotate closure members. Because bearings 1350a may be exposed to a corrosive environment, they can, for example, be formed from a corrosion resistant material such as nitrided martensitic stainless steel or a ceramic material. Each shaft 1332a of a closure member 1330a (two in the embodiment illustrated in FIGS. 10A through 10D) may, for example, include two bearings 1350a positioned on shafts 1332a at opposite ends of closure members 1330a. In the illustrated embodiment, each bearing 1350a is sealed from the blood flow path by seals 1340a.

External to (or radially outward from, with reference to axis $A_1$—see FIG. 10A) bearings 1350a, at least one end of shafts 1332a includes an extending section 1332a' (which can be a part of shaft 1332a or connected thereto). Rotational activation of extending sections 1332a' results in rotation of closure members 1330a operatively connected thereto in an opening or closing direction via an activating system such as activating system 1500 illustrated, for example, in FIGS. 10A through 10D.

In the illustrated embodiment, valve support structure 1310a is formed in two sections 1312a and 1314a which are separable from each other along a plane generally perpendicular to axis $A_1$ of pump system 1300. Such a construction may facilitate assembly valve assembly 1300*a*, including the mounting of closure member shafts 1332*a* while, for example, in operative connection with associated seals 1340*a* and associated roller element bearings 1350*a* in valve support structure 1310*a*. FIG. 10B illustrates mounting of those components in section 1312*a* of valve support structure 1310*a*. In FIG. 10C, section 1312*a* is illustrated without seals 1340*a* in operative connection with shafts 1332*a* to illustrate the seatings therefor formed in section 1314*a*. Similar seatings (not shown) are formed in section 1314*a*.

In the embodiments illustrated in FIGS. 10A through 10D, closure member activating system 1500 is formed at least partially integrally with valve support structure 1310*a* of valve assembly 1300. However, the activating system can be formed separately from and in operative connection with valve assembly 1300. For example, activating system 1500 may be operatively connected to an annular connector 410 (driven by motor 320) within pump system housing 302. Activating system 1500 includes a positioning mechanism such as a positioning gear 1510 in operative connection with (for example, keyed thereto) extending sections 1332*a*' of shafts 1332*a*. A rack 1520 including teeth on two sides thereof, which are adapted to mesh with positioning gears 1520, is operatively connected between positioning gears 1510*a*. A change in the position of rack 1520 along a line generally parallel to axis $A_1$ drives positioning gears 1510 and, thereby, shafts 1332*a* and closure members 1330*a*. In that regard, rotational motion of positioning gears 1510 imparts rotational motion to extending sections 1332*a*'.

Figure 10A:
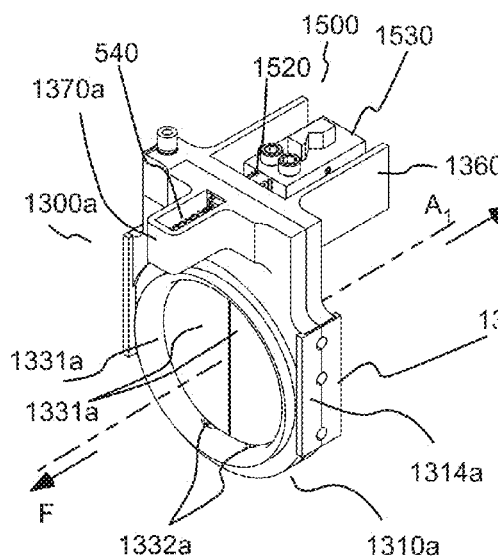
FIG. 10A illustrates a perspective view of another embodiment of a valve assembly hereof including a closure member activating system to actively move the closure members toward an open position or toward a closed position.
Figure 10B:
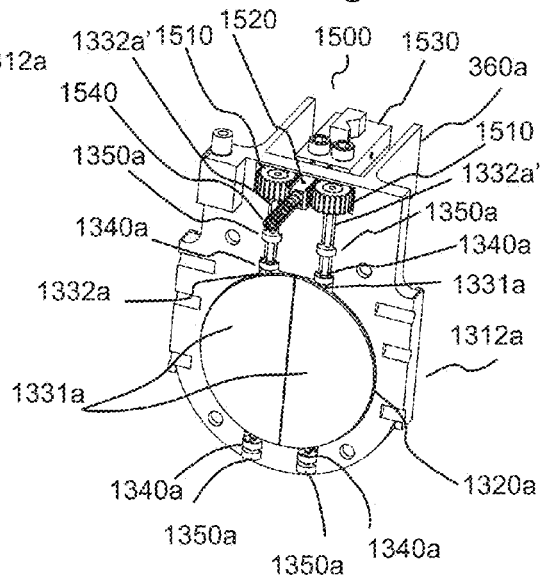
FIG. 10B illustrates a perspective view of a section of the valve assembly of FIG. 10A.
Figure 10C:
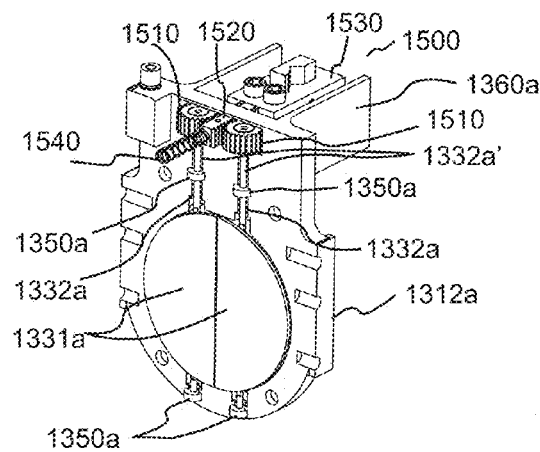
FIG. 10C illustrates another perspective view of a section of the valve assembly of FIG. 10A wherein seals have been removed.
Figure 10D:
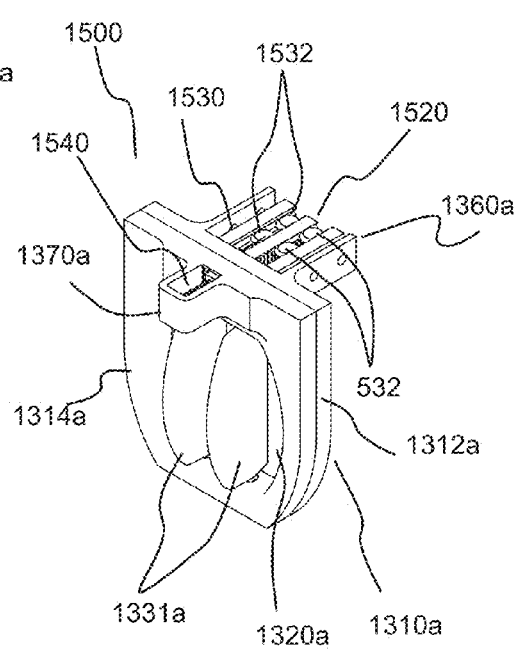
FIG. 10D illustrates a perspective view of the valve assembly of FIG. 10A with the closure member thereof in an open position.

An abutment member (not shown in FIGS. 10A through 10D, but, for example, positioned at a fixed position relative to (and within) housing 302 (with reference to pump system 300) can, for example, contact rack 1520 as valve assembly 1300*a* moves rearward (represented by arrow R in FIG. 10A) in the vicinity of the rearwardmost position of valve assembly 1300*a* to drive rack 1520 in a forward direction. Forward motion of rack 1510 rotates positioning gear 1510 on the right side (from the perspective of the viewer of FIGS. 10A through 10D) of rack 1520 in a counterclockwise direction and rotates positioning gear 1510 on the left side of rack 1520 in a clockwise direction to move closure members 330*a* toward a closed position as illustrated in FIGS. 10A through 10C. As, for example, illustrated in FIG. 10D, rack 1510 can be movable through a linear bearing 1530 which limits movement of rack 1520 to movement in a single linear direction. Each side of linear bearing 1530 may, for example, operate in the manner of a linear rolling element bearing. Each side of linear rolling element bearing 1530 may, for example, include two geared roller elements 1532. In the illustrated embodiment, linear rolling element bearing 1530 is positioned within a seating 360*a* which is attached to or formed integrally or monolithically with section 312*a*.

Rack 1520 need, for example, travel only a short distance between the positioning gears 1510 to activate closing or opening of both closure members 1330*a*. In one embodiment, positioning gears 1510 rotate closure members approximately 90 degrees from a fully open position illustrated in FIG. 10D, wherein closure members 1330*a* are oriented generally parallel to the direction of bulk flow of blood through valve opening 1320*a* to a fully closed position as illustrated in FIGS. 10A through 10C, wherein closure members 1330*a* are oriented generally perpendicular to the direction of bulk flow of blood through opening 1320*a*.

As described above in connection with valve assembly 1300, pressure from the flow of blood through valve opening 1320*a* (particularly during rearward movement of or the backstroke of valve assembly 1300*a*) tends to force closure members 1330*a* to an open position. However, a mechanism or system can be provided to, for example, cooperate with activating system 1500 to bias closure members 1330*a* to an open position or state (that is, to actively cause movement of closure members 1330*a* toward an open position or state, which is a default or normal state). Activating system 1500 may, for example, include or have in operative connection therewith a biasing mechanism or system 1540*a* that applies force to rack 1510 to cause rack 1510 to move (in the direction of arrow R in FIG. 10A) to open closure members 1330*a*. Biasing mechanism 1540*a* may, for example, bias rack 1510 to move sufficiently to rotate closure members 1330*a* (via positioning gears 510) to the fully open state illustrated in FIG. 10D when valve assembly 1330*a* is in its backstroke or when, for any reason, pump system 1300 or another moving valve pump system incorporating valve assembly 1300*a* is not active (for example, because of power loss or failure of one or more components of the pump system). In the embodiment illustrated in FIGS. 10A through 10D, biasing mechanism 1540 includes a spring positioned within a seating 1370*a* attached to or formed integrally or monolithically with section 1314*a*. Biasing mechanism or system 540 assists in preventing extended blockage of the blood flow path in any circumstance.

FIG. 11 illustrates a flow chart of an embodiment of a method of operation of the external system of FIG. 1B. Referring to FIG. 11, in a number of embodiments, external system 100*a* starts by powering up system 10*a* by starting the frequency hopping clock (represented by CLK in FIG. 1B). Power is transferred by turning on primary coil 130*a* by enabling the H-Bridge driver. External system 100*a* then waits for a message from the internal system 200*a* or an over-current condition. An over-current condition may, for example, occur when the internal system 200*a* is not present. In a number of embodiments, external system 100*a* waits approximately 200 ms. If no message from the internal system 200*a* is received, system 10*a* is disabled by disabling the H-bridge driver and stopping the frequency hopping clock. External system 100*a* then waits a period of time (for example, 1 s) and tries again. If external system 100*a* receives a message from internal system 200*a*, it is analyzed and primary coil 130*a* of system 10*a* is, for example, enabled/energized if the secondary/internal voltage is too low or disabled/de-energized if the secondary/internal voltage is too high as described above. Additionally, in a number of embodiments, system 10*a* automatically activates the power transfer if primary coil 130*a* has been off for more than a determined time $T_{MAX}$, for example 5 ms, as shown in FIG. 5E. This automatic activation avoids unnecessary discharge of secondary capacitors 250*a* during low load conditions. Additionally, this automatic activation helps to reduce the ripple voltage on capacitor system 250*a*. The sequence described above and in FIG. 11 continues as long as the external system 100*a* is powered up by its battery pack.

Referring to FIG. 12, internal system 200*a* starts when capacitor system 250*a* reaches a voltage level sufficient to power up internal controller 210*a*. Internal system 200*a* sends messages to external system 100*a* using internal communication system 290*a* and the operatively connected antenna. As described above, if the voltage on capacitor system 250*a* is above a predetermined maximum threshold or below a predetermined minimum threshold, a command to alter the system status is sent by internal system 200*a*. Internal system 200*a* also automatically sends a status command every 5 ms to ensure external system 100*a* has the latest information and can confirm that internal system 200*a* is still present. This methodology is, for example, illustrated in FIG. 5E, wherein $T_{MAX}$ is the maximum time external/primary coil 130*a* will be deactivated before internal system 200*a* automatically sends a command to activate external coil 130*a* even though $V_{MIN}$ has not yet been reached. Also, in anticipation of heavy loads, internal system 200 may pre-charge internal capacitor system 250*a* to a higher voltage ($V_{BURST}$) above the normal high threshold voltage ($V_{MAX}$) to store extra energy for a short duration high current burst such as, but not limited to, the start-up current required by motor 310 or pump system 300. An ECG signal may, for example, be used to determine when it is time to activate moving valve assembly 1300*a* via motor 310. An ECG signal is communicated to internal control system 210*a*. At a point in time determined by the ECG signal, external coil 130*a* charges capacitor system 250*a* to $V_{BURST}$. Once capacitor system 250 reaches $V_{BURST}$, internal control system 210*a* initiates start-up of motor 310. The start-up motor 310/movement of moving valve assembly 1300*a* may be timed to occur only when $V_{BURST}$ is achieved. Such synchronization of the start-up current required by motor 310 or pump system 300 and $V_{BURST}$ reduces the risk of triggering the start-up current required by motor 310 or pump system 300 when the internal voltage is somewhere other than at $V_{BURST}$.

In a number of embodiments described herein, a spread spectrum power signal is used advantageously as described above and operates independently from secondary or internal system. The power signal may, for example, be factory set to a center frequency with a fixed number of channels and fix frequency bandwidth. The power signal frequency may, for example, hop through the channels without knowledge of the status of the secondary or internal system. Additionally, the use of a spread spectrum power signal does not need to contain data. In a number of embodiments, the signal is for power only and contains no data. Power may, for example, be sent via a first spread spectrum signal in a first frequency band, while data may be sent via a second spread spectrum signal in a second frequency band different from the first frequency band. In a number of embodiments, power is sent via frequency hopping spread spectrum or FHSS and data is send via direct sequence spread spectrum or DSSS.

In a number of embodiments, power is sent via a direct sequence spread spectrum (DSSS) signal which phase-modulates the external controller clock signal pseudo-randomly with a continuous string of pseudonoise (PN) code symbols called "chips". Chips have a much shorter duration than a clock pulse, meaning each clock pulse is modulated by a sequence of much faster chips. Therefore, the chip bit rate is much higher than the clock bit rate. DSSS effectively, multiplies the clock by a "noise" signal. This noise signal is a pseudorandom sequence that has a frequency higher than that of the clock signal. The resulting signal resembles white noise. A plot of the frequency spectrum transmitted has a roughly bell-shaped envelope centered on the carrier frequency, 122.5 kHz as an example. A DSSS power transfer signal can be generated by exclusive OR-ing or multipling the clock signal from the external controller 110*a* with a PN code. The resulting DSSS signal is provided to the H-Bridge Driver clock pin (CLK). In some embodiments, external system 100*a* transmits energy without data via primary coil 130*a* to the internal system 200*a*. Typically, DSSS signals are used to communicate data. This requires the PN code to be common in the transmitter and receivers of the signal. It also requires the PN code to have finite duration to modulate data onto and demodulate data from the signal. Removing the data from the signal allows the DSSS signal used to transfer power to use a truly random signal with infinite duration, i.e. the PN code is never repeated. The resulting DSSS signal transfers energy continuously across a frequency bandwidth meaning the EMI potential from the system described herein is minimize Stated a different way, the system described herein simultaneously transmits a frequency envelop which contains multiple frequency components.

Another way to generate the spread spectrum signal is to use spread spectrum clocking. A spread spectrum clock may be generated by taking the clock and modulating it with a spreading signal such as a triangle wave signal (linear) or a Hershey kiss signal (non-linear).

In a number of embodiments described herein, a tuned primary coil is used to transfer magnetic energy wirelessly to a tuned secondary coil. The magnetic energy may, for example, be spread spectrum magnetic energy. The magnetic energy may, for example, be produced at a first frequency for a first time period and followed by magnetic energy produced at a second frequency for a second time period. The magnetic energy may, for example, be produced with direct-sequence-modulated spread spectrum with $((\sin x)/x)^2$ frequency spectrum, centered at the carrier frequency.

In a number of embodiments, the internal system 200*a* may include a second energy storage device or system 1250*a* (see FIG. 1A) in addition to first energy storage device or system 250*a* (for example, capacitor system 250*a*), which may, for example, be a rechargeable battery. Energy storage device 1250*a* is not meant to power the internal system during typical use/operation. In typical operation (in the first state of internal system 200*a*), all energy required by internal system 200*a* is transferred from the external system 100*a*. There may, however, be instances where external system 100*a* must be removed or powered down. As an example, the patient may remove external system 100*a* during a shower or bath. As another example, the patient may be required to power down external system 100*a* during air travel. Under those circumstances, internal system 200 may be placed in a second state wherein energy storage device 1250*a* may take over powering internal system 200*a* for short durations. Internal system 200*a* may, for example, operate at full power (normal operation) or may operate at a reduced power level (reduced function mode) when powered by energy storage device 1250*a*. The use of energy storage device 1250*a* may be limited to short duration infrequent events, which maximize the lifetime of internal energy storage device 1250*a*. This mode of operation overcomes shortcomings of currently available systems and avoids the need for maintenance to internal system 200*a* every couple of years (that is, surgical removal of an aged rechargeable battery pack). When used as described herein, internal secondary energy storage device may be designed to have lifetime of seven to ten years or more. Energy storage device 1250*a* may, for example, be a rechargeable Li-ion battery capable of powering internal system 200*a* for a period of time in the range of 5 minutes to two hours or any range therebetween (for example, in the range of 20 minutes to 1 hour). In systems wherein a rechargeable battery is used to power an implanted device or system such as a blood flow assist pump system continuously or at all times, a much larger battery will be required than an internal battery used in the systems hereof. In that regard, as internal batteries hereof are used only periodically, upon instructions from, for example, external system 100*a*, and for period of time ranging from, for example, 5 minutes to 2 hours or any range therebetween, significantly smaller batteries may be used than required in systems using a dedicated, continuously used battery. After a situation requiring the use of energy storage device 1250, external system 100*a* is replaced/reactivated to resume normal operation. Additionally, energy storage device 1250*a* is recharged by external system 100*a*. In a number of embodiments, energy storage device 1250 may be maintained at a state of charge less than full charge to help increase the lifetime of energy storage device 1250*a*. In that regard, deep discharges and storage or operation at full charge have a negative impact on battery lifetime and performance. The patient may be required to notify external unit 100*a* that external unit 100*a* will be removed or powered down. After such notification, the patient may be required to wait a predetermined time to allow external unit 100*a* to charge internal energy storage device 1250*a* to full charge. As an example, an internal Li-ion battery may be maintained at 40-50% charge state. The patient may, through a user interface on the external unit 100*a*, notify control system 110*a* of external unit 100*a* that external unit 100*a* will be removed or powered down. The patient may be required to wait, for example, 20-30 minutes before removing or powering down external unit 100*a* to allow the internal Li-ion battery to charge to 100% capacity. Additionally, the patient may provide information to external unit 100*a* to inform of the duration of the removed or powered down event. For short duration events, internal energy storage device 1250 may not recharge to 100% capacity which minimize the required wait time.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A system, comprising:
    an implantable pump system for assisting blood flow in a patient comprising: a drive system and an energy transfer system to provide energy to the drive system, the energy transfer system comprising:
        an external system comprising a power source and an external coil, and
        an internal system comprising an internal coil adapted to receive transcutaneous energy transmitted from the external coil, the internal system having at least a first state wherein energy transmission from the external coil is required to provide operational power to the drive system, the implantable pump system having a normally open state such that blood can flow therethrough in the absence of application of energy to the drive system.

2. The system of claim 1 wherein the implantable pump system further comprises at least one moveable valve which is in the normally open state when not powered by the drive system and the internal system is unable to power the drive system to move the moveable valve through one stroke without energy transmission from the external coil when the internal system is in the first state.

3. The system of claim 1 wherein the internal system comprises a first energy storage device in electrical connection with the internal coil and the drive system, energy being provided to the drive system via the first energy storage system.

4. The system of claim 3 wherein the first energy storage system comprises no battery.

5. The system of claim 3 wherein the first energy storage system comprises a capacitor system.

6. The system of claim 3 wherein the first energy storage is capable of storing no more than 260 Joules of energy.

7. The system of claim 3 wherein the external system comprises an external control system in operative connection with the power source and the external coil and the internal system comprises an internal control system in operative connection with the first energy storage system and the internal coil.

8. The system of claim 7 wherein in the external system further comprises an external communication system in operative connection with the external control system, and the internal system further comprises an internal communication system in operative connection with the internal control system.

9. The system of claim 8 wherein the internal communication system is adapted to wirelessly transmit a signal to the external communication system to provide information related to a voltage of the first energy storage system, the external system being adapted to cause the power source to energize the external coil upon receiving information transmitted from the internal communication system indicating that the voltage is at least as low as a lower threshold value to charge the first energy storage system and to de-energize the external coil upon receiving information transmitted from the internal communication system indicating that the voltage is at least as high as a higher threshold value.

10. The system of claim 9 wherein the external control system is adapted to cause the power source to energize the external coil after a determined maximum time period that the external coil has not been energized regardless of whether or not the voltage is at least as low the lower threshold value.

11. The system of claim 9 wherein the external control system is adapted to cause the power source to energize the external coil in a manner to result in the voltage being greater than the higher threshold value in anticipation of a required high energy load.

12. The system of claim 9 wherein the external communication is adapted to transmit to or receive informational signals from the internal communication system via at least one of an external radio or the external coil, and the internal communication system is adapted to transmit information signals to or receive signals from the external communication system via at least one of an internal radio or the internal coil.

13. The system of claim 12 wherein, when information signals are transmitted between the external coil and the internal coil, the information signals are transmitted within a frequency range different from a frequency range at which energy is transmitted from the external coil to the internal coil.

14. The system of claim 8 further comprising a monitoring system to measure a variable related to current draw by the external coil to provide information to the patient regarding position of the external coil relative to the internal coil based at least in part on the measured variable related to current draw on the external coil.

15. The system of claim 14 wherein the monitoring system to measure a variable related to current draw on the external coil comprises a current sensor in electrical connection with the external coil and in communicative connection with the external control system.

16. The system of claim 3 wherein the internal system further comprises a second energy storage system, and the internal system has a second state wherein energy is drawn from the second energy storage system to provide energy to the drive system.

17. The system of claim 16 wherein the second energy storage system stores sufficient energy to provide operation power to the drive system without transfer of energy from the external coil.

18. The system of claim 17 wherein the second energy storage system comprises an internal rechargeable battery.

19. The system of claim 18 wherein the internal system is placed in the second state upon instructional information being transmitted from the external control system via the external communication system to the internal control system via the internal communication system.

20. The system of claim 19 wherein the external system is adapted to allow the patient to manually cause the internal system to be in the second state.

21. The system of claim 18 wherein no energy is drawn from the rechargeable battery to provide energy to the drive system in the first state.

22. The system of claim 21 wherein the rechargeable battery is adapted to power the drive system for a period of time in the range of 5 minutes to 2 hours.

23. The system of claim 1 wherein, when the external coil is energized, energy is transmitted from the external coil to the internal coil over a range of frequencies.

24. The system of claim 23 wherein, when the external coil is energized, energy is transmitted from the external coil to the internal coil in a range of frequencies under control of a spread spectrum algorithm.

25. The system of claim 24 wherein the nominal transmission frequency is between 50 and 500 kHz.

26. The system of claim 25 wherein the spread spectrum algorithm is a frequency hopping spread spectrum algorithm.

27. The system of claim 25 wherein the spread spectrum algorithm is a direct sequence spread spectrum algorithm.

28. The system of claim 25 having a Q factor less than 10.

29. The system of claim 24 wherein the range of frequencies extends from approximately 120 kHz to approximately 130 kHz.

30. The system of claim 29 wherein the range of frequencies extends from approximately 120 kHz to approximately 126 kHz.

31. The system of claim 24 wherein the external system and the internal system are adapted such that a change of frequency of energy transmitted from the external coil to the internal coil of +/−10% results in a change in transfer efficiency of no greater than 10%.

32. The system of claim 24 wherein the external system and the internal system are adapted to operate as a band-pass filter.

33. The system of claim 32 wherein tuning capacitors and leakage inductances form series elements of the band-pass filter and magnetizing inductance forms a shunt element.

34. The system of claim 33 further comprising fixed tuning capacitors.

35. The system of claim 24 wherein energy is transmitted from the external coil to the internal coil in the range of frequencies with a set resonant frequency of the external coil and a set resonant frequency of the internal coil.

36. The system of claim 24 wherein a resonant frequency of at least one of the internal coil or the external coil is tunable.

37. The system of claim 1 wherein the external system comprises an external communication system and the internal system comprises and internal communication system, wherein the external communication is adapted to transmit to or receive informational signals from the internal communication system via at least one of an external radio or the external coil, and the internal communication system is adapted to transmit information signals to or receive signals from the external communication system via at least one of an internal radio or the internal coil.

38. The system of claim 37 wherein the internal communication system is adapted to transmit a periodic status signal to confirm operability of at least a portion of the internal system.

39. The system of claim 1 wherein the power source consists of a single rechargeable battery pack.

40. The system of claim 39 wherein the battery pack comprises a plurality of lithium ion battery cells.

41. The system of claim 1 wherein the external coil is energized at a voltage of sufficient amplitude to provide an efficiency of at least 75%.

42. A method of assisting blood flow in a patient, comprising:
    placing an implantable pump system in fluid connection with a blood vessel, the implantable pump system comprising a drive system and an energy transfer system to provide energy to the drive system, the energy transfer system comprising,
    an external system comprising a power source and an external coil and
    an internal system comprising an internal coil adapted to receive transcutaneous energy transmitted from the external coil, the implantable pump system having a normally open state such that blood can flow therethrough in the absence of application of energy to the drive system; and
    operating the internal system in a first state wherein energy transmission from the external coil is required to provide operational power to the drive system.

* * * * *